(12) United States Patent
Chakeres

(10) Patent No.: US 6,261,299 B1
(45) Date of Patent: Jul. 17, 2001

(54) STEREOTACTIC APPARATUS AND METHODS

(75) Inventor: Donald W. Chakeres, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 09/449,809

(22) Filed: Nov. 26, 1999

(51) Int. Cl.[7] ................................................. A61B 19/00
(52) U.S. Cl. ............................................................ 606/130
(58) Field of Search ............................. 606/130; 600/429

(56) References Cited

U.S. PATENT DOCUMENTS

| | | |
|---|---|---|
| 4,638,798 | 1/1987 | Sheldon et al. . |
| 4,722,336 | 2/1988 | Kim et al. . |
| 4,750,487 | 6/1988 | Zanetti . |
| 5,053,042 | 10/1991 | Bidwell . |
| 5,142,559 | 8/1992 | Wielopolski et al. . |
| 5,147,372 | 9/1992 | Nymark et al. . |
| 5,309,913 | 5/1994 | Kormos et al. . |
| 5,383,454 | 1/1995 | Bucholz . |
| 5,426,685 | * 6/1995 | Pellegrino et al. .................... 378/87 |
| 5,437,280 | 8/1995 | Hussman . |
| 5,447,154 | 9/1995 | Cinquin et al. . |
| 5,499,989 | * 3/1996 | LaBash ................................ 606/130 |
| 5,628,315 | 5/1997 | Vilsmeier et al. . |
| 5,678,549 | 10/1997 | Heywang-Koebrunner et al. . |
| 5,690,108 | 11/1997 | Chakeres . |
| 5,830,219 | * 11/1998 | Bird et al. ............................. 606/130 |
| 5,913,863 | * 6/1999 | Fischer et al. ........................ 606/130 |
| 5,971,998 | * 10/1999 | Russell et al. ........................ 606/130 |

OTHER PUBLICATIONS

Orel et al., Staging of Suspected Breast Cancer: Effect of MR Imaging and MR–guided Biopsy, Radiology 1995; 196:115–122.

Stelling, Breast Cancer Staging with Contrast Material–Enchanced MR Imaging: Should it Change Patient Treatment?, Radiology 1995; 196:16–18.

Mumtaz et al., Laster Therapy for Breast Cancer: MR Imaging and Histopathologic Correlation, Radiology 1996; 200: 651–658.

Orel et al., MR Imaging–Guided Localization and Biopsy of Breast Lesions: Initial Experience, Radiology 1994; 193: 97–102.

* cited by examiner

*Primary Examiner*—Jeffrey A. Smith
*Assistant Examiner*—Eduardo C. Robert
(74) *Attorney, Agent, or Firm*—Standley & Gilcrest LLP

(57) ABSTRACT

The present invention includes stereotactic vectors using no electronic calculations and imaging, diagnostic and treatment techniques. The invention also includes machines or instruments using those aspects of the invention. The present invention also includes methods and processes using the devices of the present invention. The methods and devices of the present invention may be used in stereotactic-guided percutaneous breast biopsies, an alternative to open, surgical breast biopsy.

22 Claims, 23 Drawing Sheets

STEREOTACTIC APPARATUS AND METHODS

TECHNICAL FIELD OF THE INVENTION

This invention relates generally to apparatus and methods useful in scientific research and interventional medicine, and useful in the visualization and analysis of organic tissues and bodies; and to research into the cause and symptoms of disease, its diagnosis and treatment. The invention particularly concerns apparatus which may be advantageously utilized by a researcher, physician or health care professional, in cooperation with types of medical imaging equipment, such as computed tomography (CT) imaging equipment or magnetic resonance (MR) imaging equipment, plain film or fluoroscopy. The invention may be utilized to conveniently and accurately aid in timely (real time), manually, truly, and physically accomplishing the steps of locating, vectoring, and inserting an object such as a probe or other needle-like medical device at, toward, and in a patient's targeted anatomic feature, particularly in the breast of a female patient for purposes of performing a breast biopsy.

BACKGROUND OF THE INVENTION

This invention relates to a stereotactic device for use with an imaging apparatus (such as magnetic resonance, CT imaging, and fluoroscopy) useful in the visualization and analysis of organic tissues and bodies, and to research into the cause and symptoms of disease, its diagnosis and treatment.

It is often necessary to sample or test a portion of tissue from humans and other animals, particularly in diagnosing and treating patients with tumors. When a physician establishes that suspicious circumstances exist, a biopsy is typically performed to determine whether the cells are cancerous. A biopsy may be accomplished by an open or percutaneous technique. Open biopsy removes part or all of the potentially cancerous mass. Percutaneous biopsy is usually done with a needle-like instrument and may be either a fine needle aspiration (FNA) or a core biopsy. In FNA biopsy, individual cells or cell clusters are obtained for cytologic examination. In core biopsy, a core or fragment of tissue may be obtained for histologic examination that may be accomplished utilizing a frozen section or paraffin section.

The biopsy done depends a lot on the surrounding circumstances. No single procedure is ideal for all cases.

To properly diagnose a questionable mass, tissue is needed from an organ or lesion within the body. Usually only part of the organ or lesion needs to be examined. The sample extracted must, however, be representative of the organ or lesion as a whole. In the past, surgery was necessary to locate, identify and remove the sample. With the advent of medical imaging equipment such as x-rays, fluoroscopy, ultrasound, and magnetic resonance imaging, it became possible to identify tiny abnormalities embedded deep within the body. Definitive characterization, though, still requires adequate sampling to characterize the histology of the organ or lesion.

As an example, mammography can often identify non-palpable breast abnormalities earlier than they could be diagnosed by physical examination. Although most non-palpable breast abnormalities are benign, some may be malignant. If breast cancer can be diagnosed before it becomes palpable, the subsequent mortality rate can be reduced. However, it is often difficult to determine whether or not pre-palpable breast abnormalities are malignant, as some benign lesions have mammographic features which mimic malignant lesions and some have features which mimic benign lesions.

To reach a definitive diagnosis, tissue from within the breast must be removed and examined under a microscope. Prior to the late 1980's, reaching a definitive tissue diagnosis for non-palpable breast disease required a mammographically-guided localization, either with a wire device, visible dye, or carbon particles, followed by an open, surgical biopsy utilizing one of these methods to guide the surgeon to the non-palpable lesion within the breast.

In one open method of the prior art, a breast is pierced with a localization wire to position the large diameter section of the wire through the center of the lesion, acting as a temporary marker. Tissue is then removed around the area marked by the localization wire. The tissue is prepared and sectioned for evaluation. Such an open surgical breast biopsy can have many drawbacks. Open biopsies can be disfiguring, expensive, and are imperfect. Any of a number of possible errors may lead to an incorrect diagnosis of a lesion. Open surgical biopsies also carry a small mortality risk due to the risk of anesthesia, and a moderate morbidity rate including bleeding, infection, and fracture or migration of the localizing wire. In cases where multiple lesions are present, a surgeon may be reluctant to biopsy each lesion due to the large tissue mass that must be extracted from the breast. The most convenient lesion is typically taken which results in an incomplete diagnosis. Finally, surgical breast biopsies are extremely common. In the United States alone it is estimated that open, surgical breast biopsies are performed on over 500,000 women annually. A less invasive alternative has long been sought.

In 1988, two stereotactic guidance systems were modified to allow the guiding portion of each system to accommodate spring powered devices. In 1989, free-hand ultrasound guidance techniques were developed to guide the stereotactic guidance systems to breast lesions seen by ultrasound. With the introduction of stereotactic and ultrasound guided percutaneous breast biopsies, an alternative to open, surgical breast biopsy was obtained.

In the use of magnetic resonance imaging ("MRI") for breast biopsies, there is a serious problem with the interventional procedures. The problem is that the probe cannot be seen, and therefore its location is unknown at the moment before it is to enter the patient. This is one of the most important reasons why MRI has not been used extensively for interventional procedures.

There are many imaging stereotactic devices currently available. Despite the incredible power of existing imaging technologies however, very few procedures are actually done using the existing technology in a routine clinical setting. There are several reasons for the lack of general acceptance of these devices in existing markets.

Most of the systems are expensive, and normally this expense cannot be justified in terms of usage or benefit for the large capital investment required. Physicians and hospitals are generally not prepared in today's economic climate to make a large investment for a system that may only be used intermittently and may become quickly outdated.

Most existing systems are electronic and use optical and computer interfaces. The majority of these systems do not function in a real-time setting, but rather use special post-processed acquired image information. This information is then used to direct the procedure at a different time and place.

Many of the systems are imager proprietary or dependent, so it is possible that only a few units may be able to use a specific technology. Though these systems claim to have very high real-space accuracy, in reality, they have only limited real-space correlation since there is no live (real-time) imaging to confirm the progress of the procedure.

Most stereotactic units are complex and have multiple components. Some of the systems envelop the patient, for example, through the use of head frames that are bolted directly to the skull. If there is any change in the components of such a rigid system at the time and place of the actual intervention, the previously obtained information that forms the basis for the intervention is no longer valid. These systems also rely on gathering many images to direct the operation, rather than needing only a few. Because of this, the process can be very slow, since a large amount of data needs to be acquired to direct the process.

A number of existing stereotactic systems utilize fiducials that are placed on the patient or the stereotactic frame. These are image-conspicuous markers that are seen in the image space and real-space. Utilizing this information, the virtual reality space depicted on the images is fused with the real-space.

There are a number of devices that attach directly to the scanner, but these are generally cumbersome and have not been used extensively.

There are also a few systems that use very limited vector trajectories (of only a few angles). These are of little value since the limited number of approaches they provide to the target may not be enough to address the complicated anatomy, therapeutic devices and goals of a variety of procedures.

Currently there are a number of rapid CT or MRI data acquisition systems available, but they have the disadvantages of being proprietary and of exposing the patient and operator to increased radiation dosage. These CT systems are analogous to fluoroscopy.

There are a few combined CT and fluoroscopic stereotactic systems. These have the potential to be very versatile, but they are complex proprietary systems. There are also a number of open magnet designs, but these are limited by vendor design. Critical information used to direct the procedure or intervention is based on artifacts from the needle or probe rather than on accurate real-time real-space information. The inherent imaging problems created by these artifacts limit the accuracy of these devices. The image quality of the fast imaging systems in general is not as good as routine imaging techniques.

FIG. 1 is a schematic of an enveloping frame that is used for head stereotactic systems of the prior art. The vertical lines 1 of the box represent the vertical struts, the horizontal lines 2 are crossing members used to define the section plane, the angled lines 3 represent cross-members and the sphere 4 is the target. This frame is bolted or rigidly fixed to the patient and then imaged with many sections. The information gathered is used at a later time and place. Without real-time real-space confirmation during the intervention, there is no absolute confirmation that the previously determined plan is actually being correctly implemented.

FIG. 2 is a schematic of an image obtained from such a fixed frame rigid system. The vertical members 1 are seen at the corners of the square, and the cross-members 3 are used to define the slice location and the target 4. There is no intuitive information that an operator can use to confirm that the information is accurate. Typically, a second system is used to actually execute the procedure at a later time with no real-time real-space confirmation of the previously obtained plan.

FIG. 3 shows an example of an MRI image 5 showing the use of a fixed frame stereotactic unit used for head imaging. The head 6 appears in the center of the image, with the target labeled in the left temporal bone. Also visible are the rods 7 (such as horizontal, vertical and cross-members 1, 2 and 3 shown in FIG. 2) surrounding the skull of the patient as a fixed device. The information is acquired by taking multiple images that must be post-processed.

There are a number of limitations to this type of device. The constituent support tubes are necessarily relatively large (in order to support the static arrangement), and thus cause a certain degree of inherent error in the system. The image shown is a single image that provides no real-time information that an operator might use during an image-monitored procedure. Also, a further error factor arises because the tubes are relatively distant from the target site, and the image itself is not without distortion, making the system distortion sensitive. Also, if the subject is moved, the system cannot be readily realigned.

A number of computer-based systems' disadvantages have been mentioned. The most important of these is that they provide no real-time confirmation at the actual time of intervention. All of these systems use specially acquired post-processed images that assume that the virtual reality of the previously obtained imaging information and the true reality at the time of the actual intervention are identical. These systems are expensive, large, and can only be used in select locations.

There remain problems associated with fast, open, and combined technology systems. All are expensive, vendor specific and, as such, are limited to only a few sites. They are such complicated systems that any minor problem can render them useless, for example, if the batteries on an LED stop working. They have limited real-space accuracy since they have problems with partial volume averaging and other imaging artifacts. Using these systems it may be difficult to track more than one device being used at a time.

Accordingly, the criteria for an improved stereotactic device includes:

1. Accuracy in the form of mm level control and live image confirmation.
2. Ability to make rapid adjustments (preferably by remote control), and the use of a single image.
3. Flexibility in the form of multiple dimension adjustability, and the accommodation of a wide variety of probes.
4. Intuitive use through clear, non-computer-generated interpretation of electronic image information.
5. Simple construction; a device that may be compact enough to fit within the imaging system next to the patient and inexpensively constructed, and may be of disposable materials.
6. Applicability independent of site and imaging device.

Accordingly, there remains a need for relatively inexpensive stereotactic devices that may be used with a wide variety of imaging systems for the performance of varied procedures, and that may be used with any number of invasive devices and techniques.

Although the present invention is presented against the backdrop of certain imaging techniques and devices, and the problems faced in using them, the present invention is not limited to use with these techniques and devices. Rather, the present invention may find application in other health care, research, and industrial applications.

SUMMARY OF THE INVENTION

The present invention includes stereotactic devices that do not require electronic calculations, and imaging, diagnostic and treatment techniques.

In broadest terms the stereotactic device of the present invention comprises: (I) a lower plane portion defining a lower plane, the lower plane portion comprising at least one pair of angled members of an imager-conspicuous material, each of the pairs of angled members defining an angle, preferably of about 53 degrees; and (ii) an upper plane portion defining a plane orthogonal to and above the lower plane portion, the upper portion comprising: (1) a framing structure; (2) a first and second plate, or first and second movable alignment structure, comprising an imager-inconspicuous material, the first and second plate or alignment structure adapted to slide back and forth in the framing structure along the lower plane portion, the first and second plate or alignment structure each comprising a pair of parallel imager-conspicuous members, each of the pairs of imager-conspicuous members preferably separated by a different distance, the pairs of parallel imager-conspicuous members aligned on the plates or alignment structures such that the intersection of one of the imager-conspicuous members on the first plate or alignment structure with one of the imager-conspicuous members on the second plate or alignment structure forms an angle (preferably approximately 53 degrees, each $\Delta=26.5$ degrees from horizontal), the first and second plates or alignment structures having an open passage extending therethrough and at the intersection between the pairs of parallel image-conspicuous members through which at least portions of a probe may be passed.

The device preferably also comprises a probe alignment structure comprising an imager-inconspicuous material, the probe alignment structure located at the open passage extending through the first and second plates or alignment structures, the probe alignment structure adapted to move and reside within the open passage as a result of movement of at least one of the first and second plates or alignment structures, the probe alignment structure comprising an opening through which at least portions of a probe may be passed.

The imager conspicuous material is preferably selected from the group consisting of materials conspicuous to an imaging device, the imaging device being selected from the group consisting of cross-sectional imagers and projection imagers.

The framing structure may additionally comprise a graduated position scale to accord the vertical position of the intersection of the image conspicuous members to the horizontal movement of one of the plates.

The device may additionally comprise at least one remote actuator 100, as shown in FIG. 26, to move the first and second plates with respect to one another. The remote actuator 100 preferably comprises a device to measure its movement, the device comprising: (a) a hollow outer sleeve 104, (b) a threaded member 102 adapted to move within the sleeve, and (c) an engaging member 106 extending into the hollow outer sleeve a sufficient distance to engage the threads of the threaded member so as to permit the threaded member to be moved within the hollow outer sleeve by a turning motion of the threaded member, and the engaging member disposed with respect to the threaded member so as to permit the threaded member to be moved discrete distances approximately equal to the distance between adjacent threads within the hollow outer sleeve by direct pushing or pulling motion so as to overcome the engagement of the engaging member and the threads.

The lower plane portion may additionally comprise a rotation attachment adapted to allow the lower portion to rotate with respect to a flat surface.

The first and second plates may further comprise a graduated linear distance position scale.

The members comprising an imager-conspicuous material may be selected from the group consisting of metal members, hollow polymeric members filled with an imager-conspicuous material, and polymeric members treated with an imager-conspicuous material.

The stereotactic device may also comprise a planar compression member positioned in the framing structure so as to prevent the first and second plates from contacting a patient's skin. The planar compression member may be any appropriate member for allowing passage of a probe into a surface while preventing the surface from contacting the sliding plates, such as a perforable membrane or polymeric mesh.

Also included in the present invention is, in broadest terms, a breast biopsy system comprising: (I) a stereotactic device, the stereotactic device comprising a base portion attached to: (a) a lower plane portion defining a lower plane, the lower plane portion comprising at least one pair of angled members of an imager-conspicuous material, each of the pairs of angled members defining an angle, preferably of about 53 degrees; and (b) an upper plane portion defining a plane orthogonal to and above the lower plane portion, the upper portion comprising: (1) a framing structure; (2) a first and second plate comprising an imager-inconspicuous material, the first and second plate adapted to slide back and forth in the framing structure along the lower plane portion, the first and second plate each comprising a pair of parallel imager-conspicuous members, the pairs of parallel imager-conspicuous members aligned on the plates such that the intersection of one of the imager-conspicuous members on the first plane with one of the imager-conspicuous members on the second plate forms an angle (preferably approximately 53 degrees, each $\Delta=26.5$ degrees from horizontal), the first and second plates having an open passage extending therethrough and at the intersection between said pairs of parallel image-conspicuous members through which at least portions of a probe may be passed; and (3) an alignment structure comprising an imager-inconspicuous material, the alignment structure located at the open passage extending through the first and second plates, the alignment structure adapted to move and reside within the open passage area as a result of movement of at least one of the first and second plates, the alignment structure comprising an opening through which at least portions of a probe may be passed; (ii) a positioning structure for supporting the upper torso of a female and positioning a breast of the female, the positioning structure comprising: (a) a lower base portion, the lower base portion comprising at least one opening through which at least a portion of the breast may pass; (b) an upper supportive portion, the upper supportive portion adapted to approximately conform to the upper torso, the upper supportive portion comprising at least one opening through which at least a portion of the breast may pass; and (c) at least one supportive member connecting the upper supportive portion to the lower base portion, the supportive member adapted to maintain a distance between the lower base portion and the upper supportive portion so as to allow passage of at least a portion of the stereotactic device; and (iii) at least one flexible supportive member for shaping and supporting the breast, the supportive member adapted to be moved and shaped according to the size and shape of the breast. The flexible supportive member may be selected from the group consisting of pillows, sponges, and foams.

The present invention also includes a method for inserting a probe into subject tissue, the method comprising the steps of: (a) placing the subject tissue into an imaging device; (b) placing a stereotactic device next to the subject tissue, the stereotactic device comprising: (1) a lower plane portion defining a lower plane, the lower plane portion comprising at least one pair of angled members of an imager-conspicuous material, each of the pairs of angled members defining an angle; and (2) an upper plane portion defining a plane orthogonal to and above the lower plane portion, the upper portion comprising: (i) a framing structure; (ii) a first and second plate comprising an imager-inconspicuous material, the first and second plate adapted to slide back and forth in the framing structure along the lower plane portion, the first and second plate each comprising a pair of parallel imager-conspicuous members, the pairs of parallel imager-conspicuous members aligned on the plates such that the intersection of one of the imager-conspicuous members on the first plane with one of the imager-conspicuous members on the second plate forms an angle, the first and second plates having an open passage extending therethrough and at the intersection between the pairs of parallel imager-conspicuous members through which at least portions of a probe may be passed; and (iii) an alignment structure comprising an imager-inconspicuous material, the alignment structure located at the open passage extending through the first and second plates, the alignment structure adapted to move and reside within the open passage as a result of movement of at least one of the first and second plates, the alignment structure comprising an opening through which at least portions of a probe may be passed; (c) acquiring an image of the subject tissue and the stereotactic device so as to locate a target point in the subject tissue in the image plane, and so as to locate the intersect points of the imager-conspicuous members of the stereotactic device with the image plane; (d) adjusting one or both of the first and second plates so as to place the intersection point even with the target point, so as to form a probe vector; and (e) inserting a probe along the probe vector to the target point.

The method may also comprise the step of preparing the subject tissue for sterile handling and treatment using an appropriate surgical preparation procedure. Another step may comprise placing a pillow or other supportive member in the imaging device to support the subject tissue.

The method may additionally comprise the step of confirming the position of the probe in the target by imaging. The method may also include the step of removing a sample of the subject tissue or completing an intervention. The method may additionally comprise the step of removing the probe and all other components.

Also included in the present invention is a method for performing breast biopsy, the method comprising the steps of: (a) bringing a stereotactic device into contact with a magnetic resonance surface coil; (b) placing a pillow or other supportive member on the magnetic resonance surface coil; (c) placing the torso of a female patient upon the upper supportive structure of the magnetic resonance surface coil, allowing the breasts of the patient to suspend from the upper supportive structure through appropriate circular openings, and supporting the appropriate breast with the pillow; (d) preparing the operable area of the breast for sterile handling and treatment using an appropriate surgical preparation procedure; (e) bringing a stereotactic device into contact with the breast; (f) imaging the breast with an appropriate imaging device and locating an appropriate target in the breast; (g) measuring the relationship of an image plane of the imaging device to a base pattern of the stereotactic device; (h) if said base pattern is not parallel to the image plane, rotating the stereotactic device to bring the stereotactic device parallel with the image plane; (i) capturing another image to a computer screen so as to confirm that the base pattern is parallel to the image plane; (j) if parallel, drawing a vector on the computer screen towards the target and parallel to the base; (k) measuring the distance and direction that the sliding pattern pairs of the stereotactic device need to be moved, the measuring occurring from the midpoint between each sliding pattern pair to a chosen target vector line; (l) moving the plates of the stereotactic device to correct dimensions and in proper directions to confirm that a needle inserted in the stereotactic device is pointing at the target; (m) confirming that the needle is in the correct vector position outside the female patient on a next image, and measuring the distance from the sliding pattern pairs to the target; (n) pushing the needle the measured distance to the target; (o) confirming the needle position in the target by imaging; (p) completing the biopsy, such as through removing tissue from the breast; and (q) removing the probe and all components.

BRIEF DESCRIPTION OF THE DRAWINGS

FIG. 7.1 is an orthogonal view of the device-generated pattern, to illustrate the geometric basis of the operation of a device in accordance with one embodiment of the present invention.—has been inserted after the paragraph that describes FIG. 7.

FIG. 7a.1 is an orthogonal view of the device-generated pattern, to illustrate the geometric basis of operation of a device in accordance with one embodiment of the present invention.—has been inserted after the paragraph that describes FIG. 7a.

FIG. 7b. 1 is an orthogonal view of the device-generated pattern, to illustrate the geometric basis of operation of a device in accordance with one embodiment of the present invention.—has been inserted after the paragraph that describes FIG. 7b.

DETAILED DESCRIPTION OF THE PREFERRED EMBODIMENTS

In accordance with the foregoing summary of the invention, the following is a detailed description of a preferred embodiment of the invention, and is presently considered to be the best mode of the invention as applied.

The device of the present invention may be made of any combination of appropriate materials such as sterile, biocompatible materials (e.g., plastic, wire, tubes, catheters, diaphragms, etc.).

As described in more detail below, the device of the present invention has two main components:

1. The first component is a lower plane portion defining a lower plane. The lower plane portion preferably comprises at least one pair of angled members of an image-conspicuous material, each of the angled members defining an angle, preferably of about 53 degrees.

2. The second component is an upper plane portion defining a plane orthogonal to and above the lower plane portion. The upper plane portion preferably has three major components:
   (a) The first component is a framing structure.
   (b) The second component is a pair of image-inconspicuous plates. The first and second plates are preferably adapted to slide back and forth in the framing structure along the lower plane portion. Each plate preferably has a pair of substantially parallel imager-conspicuous members. The separation between each pair may be different so as to aid in pair identification. Alternatively, one pair may be of a different height and width than another pair for purposes of distinction. The pairs are preferably aligned on the first and second plates such that the intersection of one of the members on the first plate with one of the members on the second plate forms and angle (preferably approximately 53 degrees, $\Delta=26.5$ degrees). There is preferably a slot between each pair through which at least a portion of a medical instrument may be passed.
   (c) The third preferred component is an alignment structure made of an image inconspicuous material. The alignment structure should be of a size and shape that allows it to be held in place at the intersection of the two aforementioned slots, and be able to slide on the slots as the intersection of those slots moves. The alignment structure preferably contains an opening adapted to allow passage of at least a portion of a medical instrument.

Figure 10:
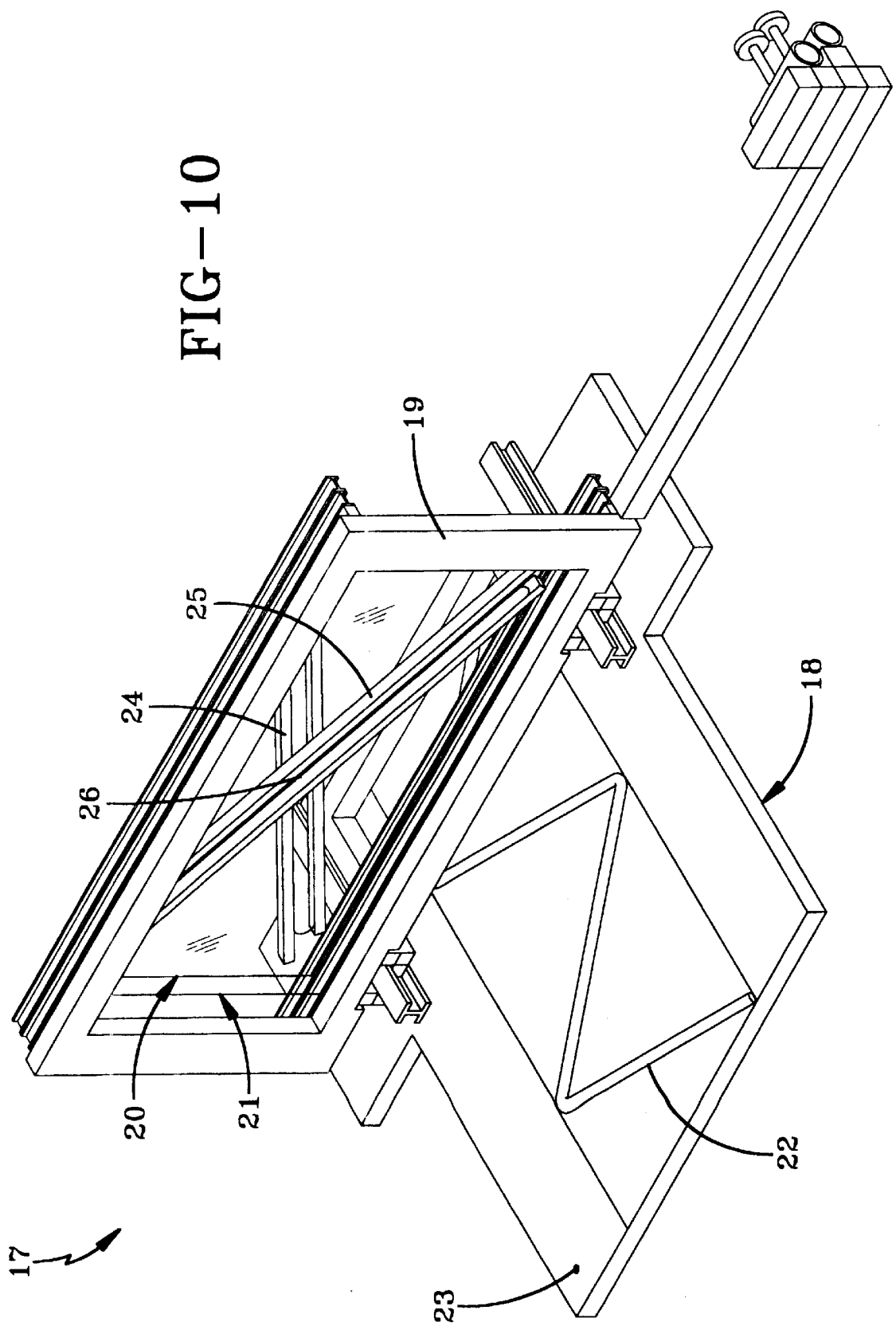
FIG. 10 is a perspective view of a stereotactic device that may be used in accordance with the present invention.

FIG. 10 shows a perspective view of a preferred stereotactic device of the present invention. The stereotactic device 17 is shown comprising a lower plane portion 18 and framing structure 19 defining an orthogonal upper plane portion. The framing structure houses the first and second plates, 20 and 21 respectively.

The lower plane portion is substantially planar, and may be made out of any appropriate substantially rigid image inconspicuous material, such as plastic. The lower plane portion preferably contains at least one pair of image conspicuous angled members 22, each angled member defining an angle of approximately 53 degrees. The lower plane portion also preferably comprises a rotation point 23 that may be attached to any appropriate structure, such as an operating table or other patient-supportive structure.

The first plate 20 in the framing structure 19 is shown comprising a first pair of image conspicuous members 24. The second plate 21 is shown with a similar second pair of image conspicuous members 25. The slots between these two pairs creates an aperture 26 at their intersection. This intersection preferably allows passage of at least part of a medical device.

Figure 11:
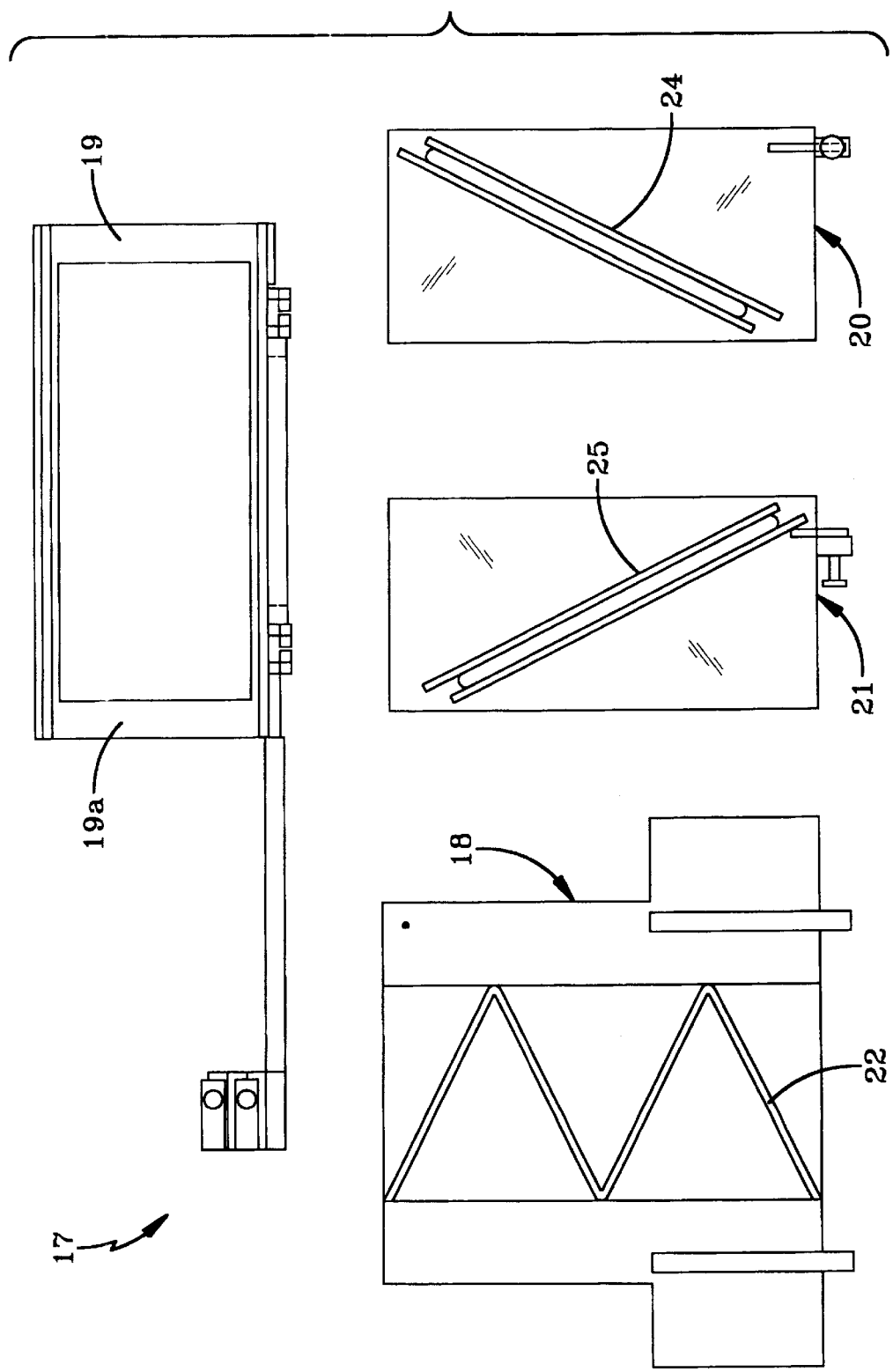
FIG. 11 is a perspective view of an unassembled stereotactic device that may be used in accordance with the present invention.

FIG. 11 shows the parts of a disassembled stereotactic device of the present invention. A preferred embodiment includes a planar compression plate 19a that is used to keep the first plate 20 and second plate 21 from contacting the target surface. The planar compression plate may be perforable, have openings, or be capable of sliding such that a probe passed through the open passage of the two plates is not blocked by the compression plate.

Figure 12:
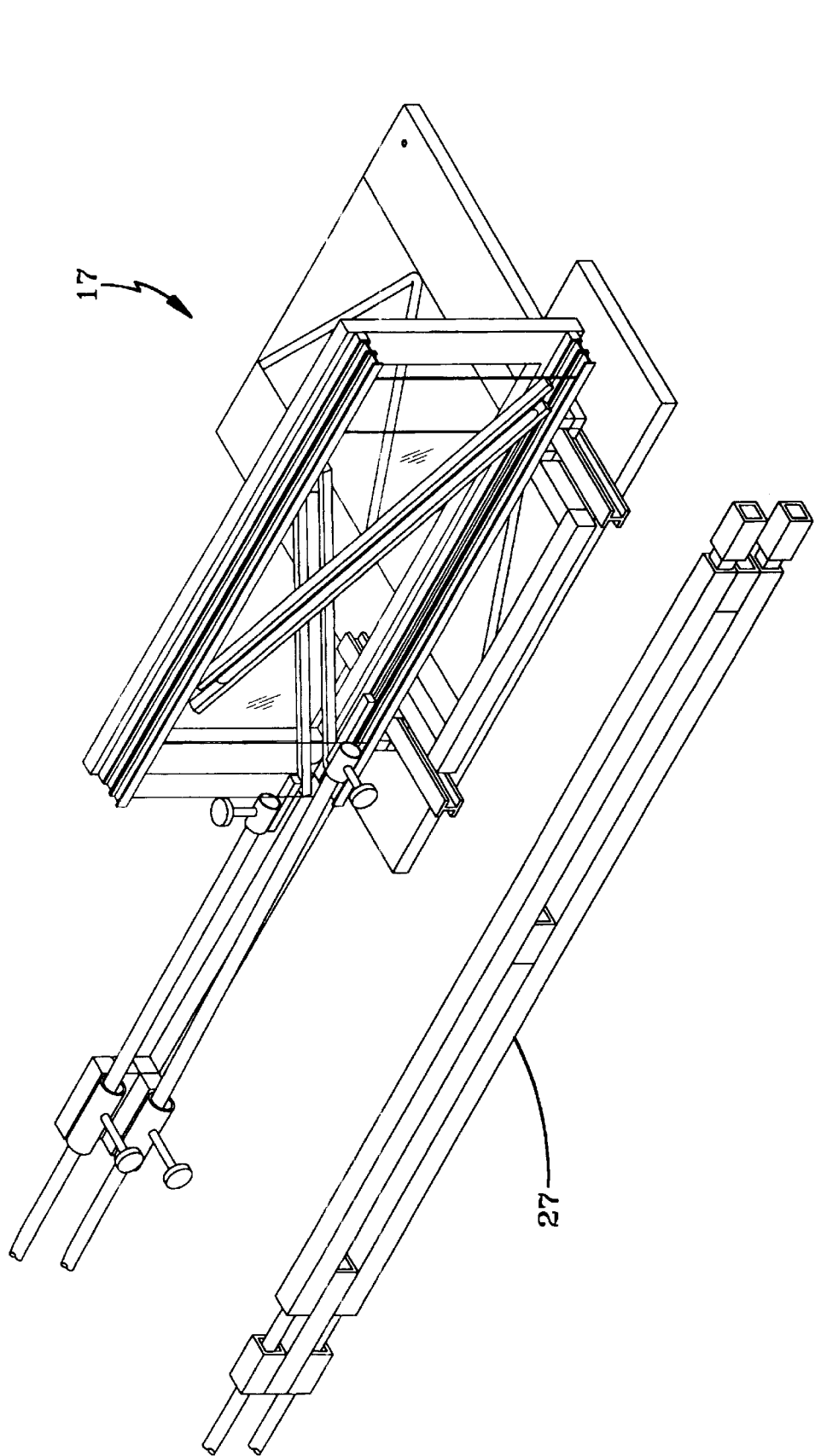
FIG. 12 is a perspective view of a stereotactic device and its associated hand control that may be used in accordance with the present invention.

FIG. 12 shows a stereotactic device 17 of the present invention along with an optional hand control 27 that may be used to remotely move the first and second plates independent of one another.

Figure 13:
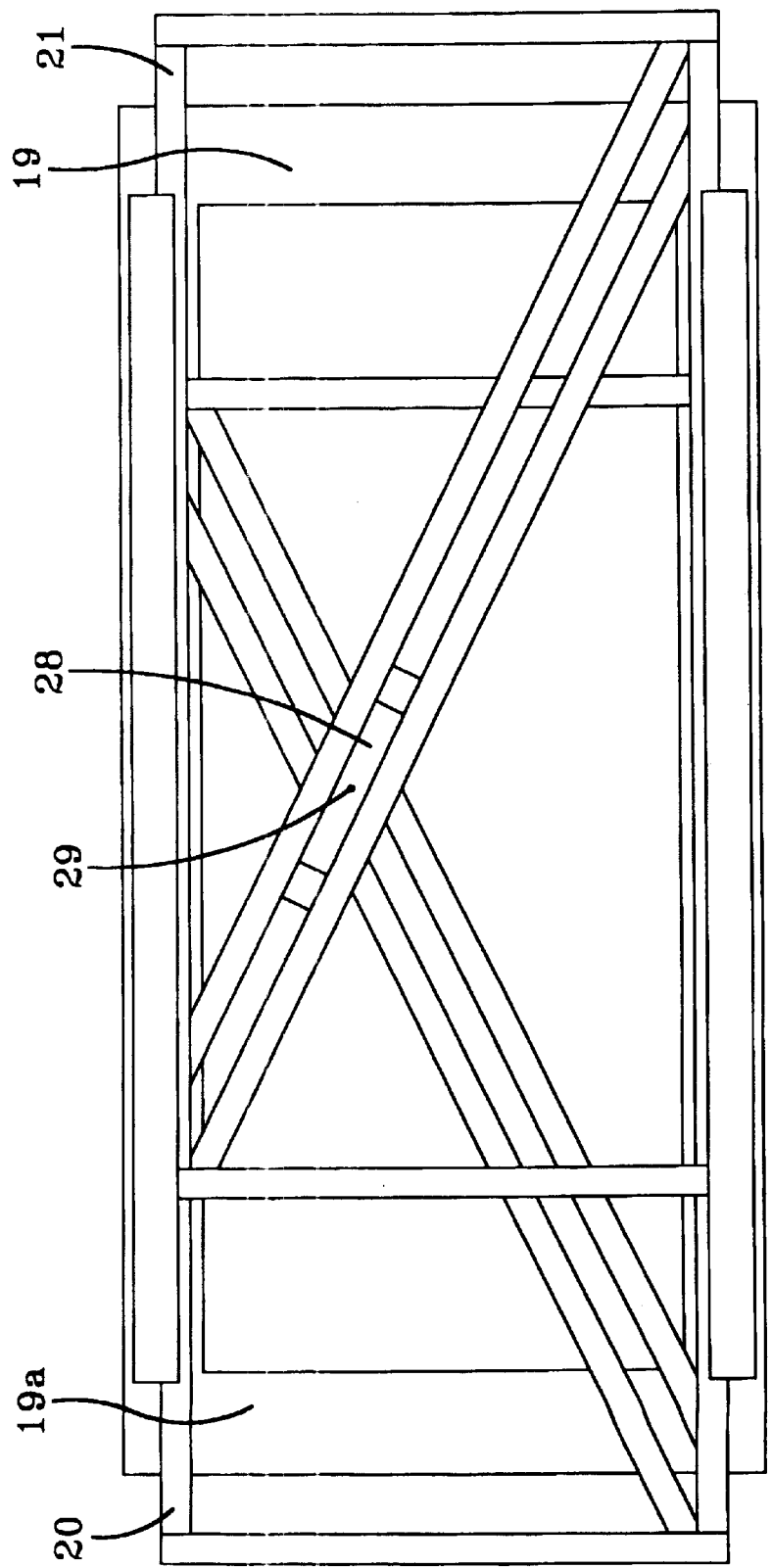
FIG. 13 is a side view of an upper plane portion that may be used in accordance with the present invention.

FIG. 13 shows the framing structure 19 containing the first plate 20, second plate 21, and planar compression member 19a. An alignment structure 28 is shown at the intersection of the slots between the pairs of image conspicuous members. The alignment structure 28 is shown comprising an opening 29 through which at least a portion of a medical instrument may be passed.

Figure 14:
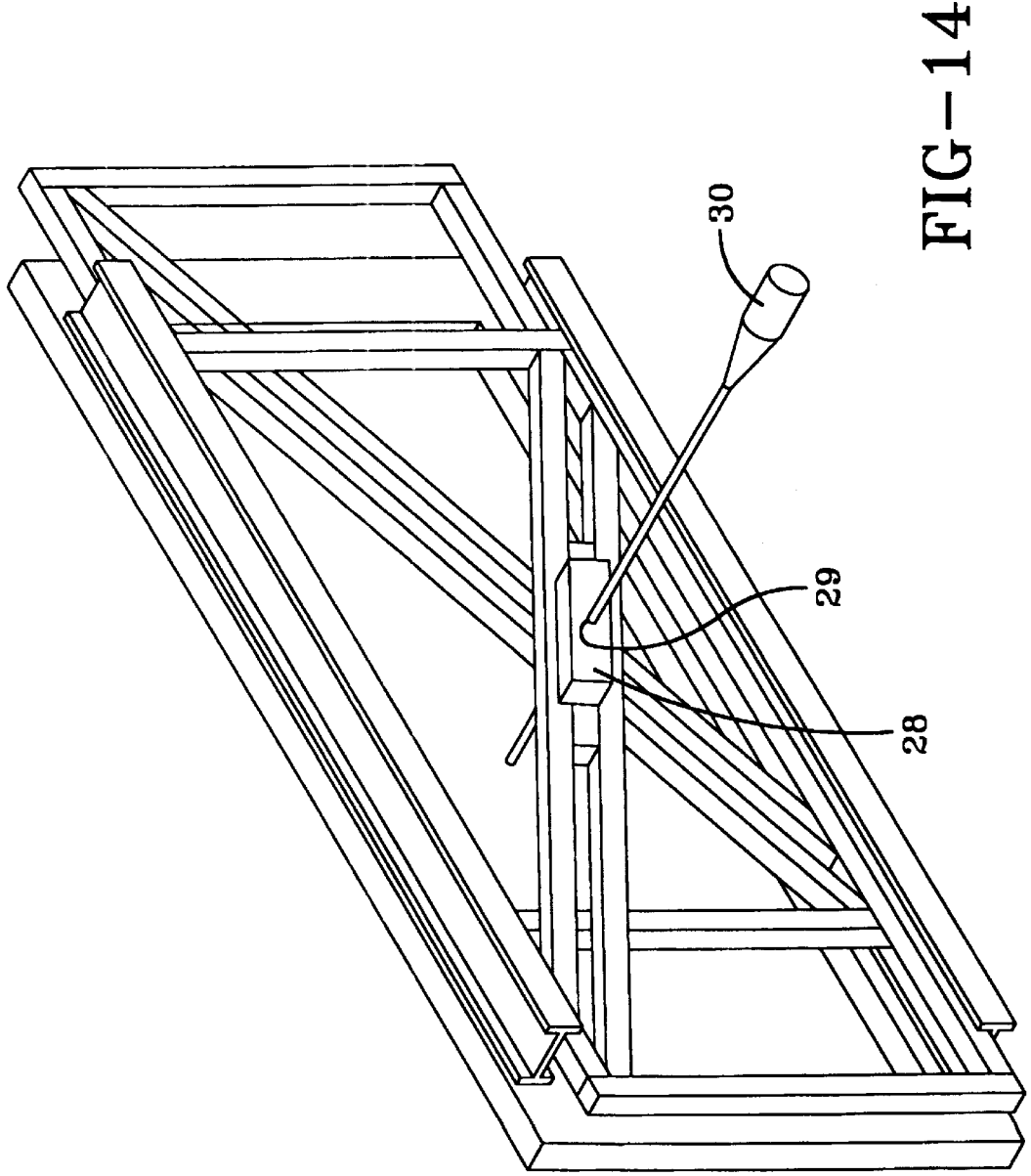
FIG. 14 is a perspective view of a medical device placed in an upper plane portion that may be used in accordance with the present invention.

FIG. 14 shows a medical probe 30 inserted into and held by the opening 29 in the alignment structure 28.

Figure 15:
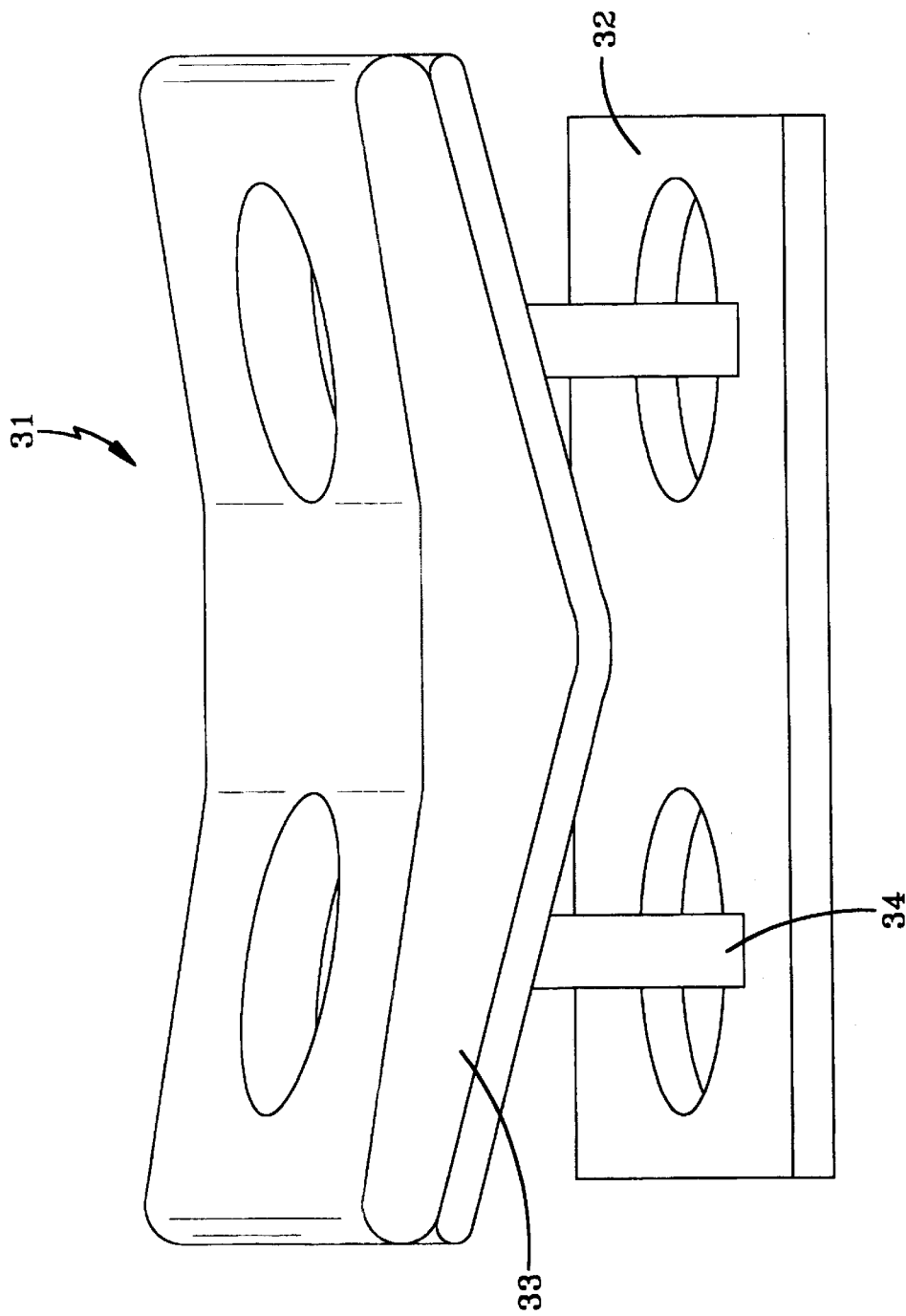
FIG. 15 is a side elevational view of a magnetic resonance surface coil that may be used in accordance with the present invention.

FIG. 15 shows a magnetic resonance surface coil 31 that may be used with a breast biopsy system of the present invention. The magnetic resonance surface coil is shown comprising a lower base portion 32, an upper supportive portion 33, and four supportive members 34 supporting the upper supportive portion 33 above the base portion 34. The upper supportive structure is shown having a semi-flexible material on its surface, such that it might conform to the torso of a patient being supported by the structure. The supportive members 34 are preferably of a length such that at least a portion of a stereotactic device of the present invention may be passed between the upper and lower portions of the magnetic resonance surface coil. The lower base portion may have an attachment device through which an attachment point of a stereotactic device may be attached.

Figure 16:
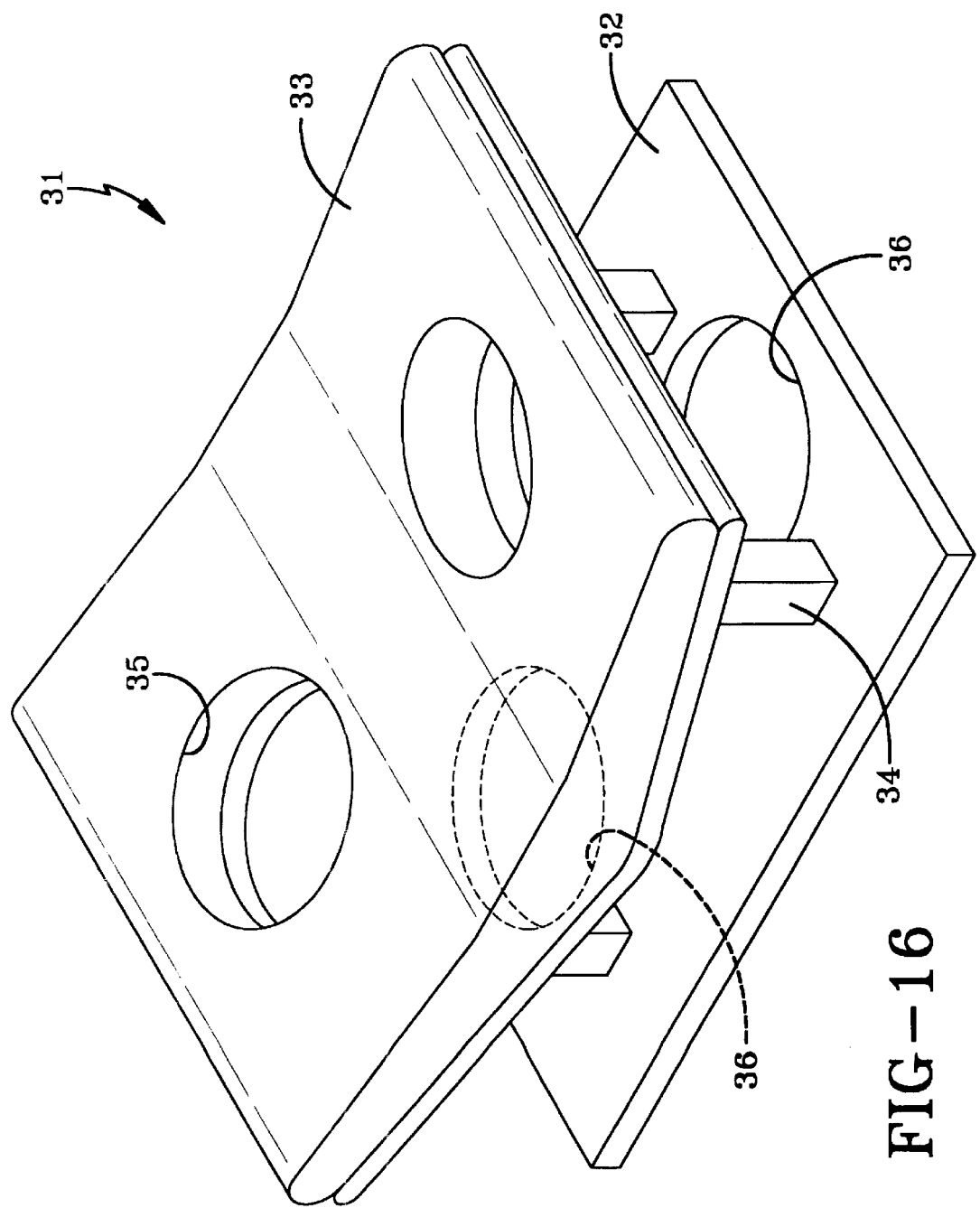
FIG. 16 is a perspective view of a magnetic resonance surface coil that may be used in accordance with the present invention.

FIG. 16 shows a perspective view of a magnetic resonance surface coil of the present invention. First circular openings 35 are shown in the upper supportive portion 33, where each opening may be of an appropriate size and shape to allow passage of at least a portion of a breast of a female patient laying face-down on the supportive structure. Similar second circular openings 36 are shown in the lower base portion 32 to allow for passage of at least a portion of a breast passed through the above first circular opening 35. Once a breast of a patient is passed through and suspended from the upper supportive portion, a stereotactic device of the present invention may then be placed or rotated near to or in contact with the breast. Once the stereotactic device is in place, a flexible supportive member such as a pillow may be used on the side of the breast opposite the stereotactic device to support and help shape the breast for biopsy.

In order to operate the device of the present invention, the following steps preferably may be followed:
1. The device is placed in contact with the magnetic resonance surface coil.
2. A pillow or other supportive member is placed on the coil.
3. The torso of a patient is placed on the upper supportive structure of the positioning structure, the breasts of the patient are allowed to suspend from the upper supportive structure through the appropriate circular openings, and the pillow is used to support the appropriate breast to be biopsied.
4. The operable area of the breast of the patient is prepared for sterile handling and treatment using an appropriate surgical preparation procedure.
5. A stereotactic device of the present invention is brought into contact with the appropriate breast of the patient.
6. The breast is imaged using an appropriate imaging device and the desired target is found.
7. The relationship of an image plane and the imaging device base pattern on the image is measured.
8. If the base pattern is not parallel to the image plane then it is rotated based on the rotation correction scale using the remote control handle.
9. Another image is acquired and viewed on a computer screen to confirm the base pattern is parallel.
10. If parallel, then a vector towards the target and parallel to the base is drawn on the computer screen.
11. The distance that the sliding patterns of the stereotactic device need to be moved and their direction is measured from the midpoint between each sliding pattern pair to the chosen target vector line.
12. The plates of the stereotactic device are then moved to correct dimensions and directions to confirm that the needle is pointing at the target, preferably by remote control.
13. The needle is then confirmed to be in the correct vector position outside the patient on a next image, and the distance from the patterns to the target is measured.
14. The needle may then be pushed the measured distance to the target using local anesthetic.
15. The needle position in the target may then be confirmed by imaging.
16. The procedure is completed, such as through removing tissue for biopsy.
17. The needle and the components are removed.

Figure 17:
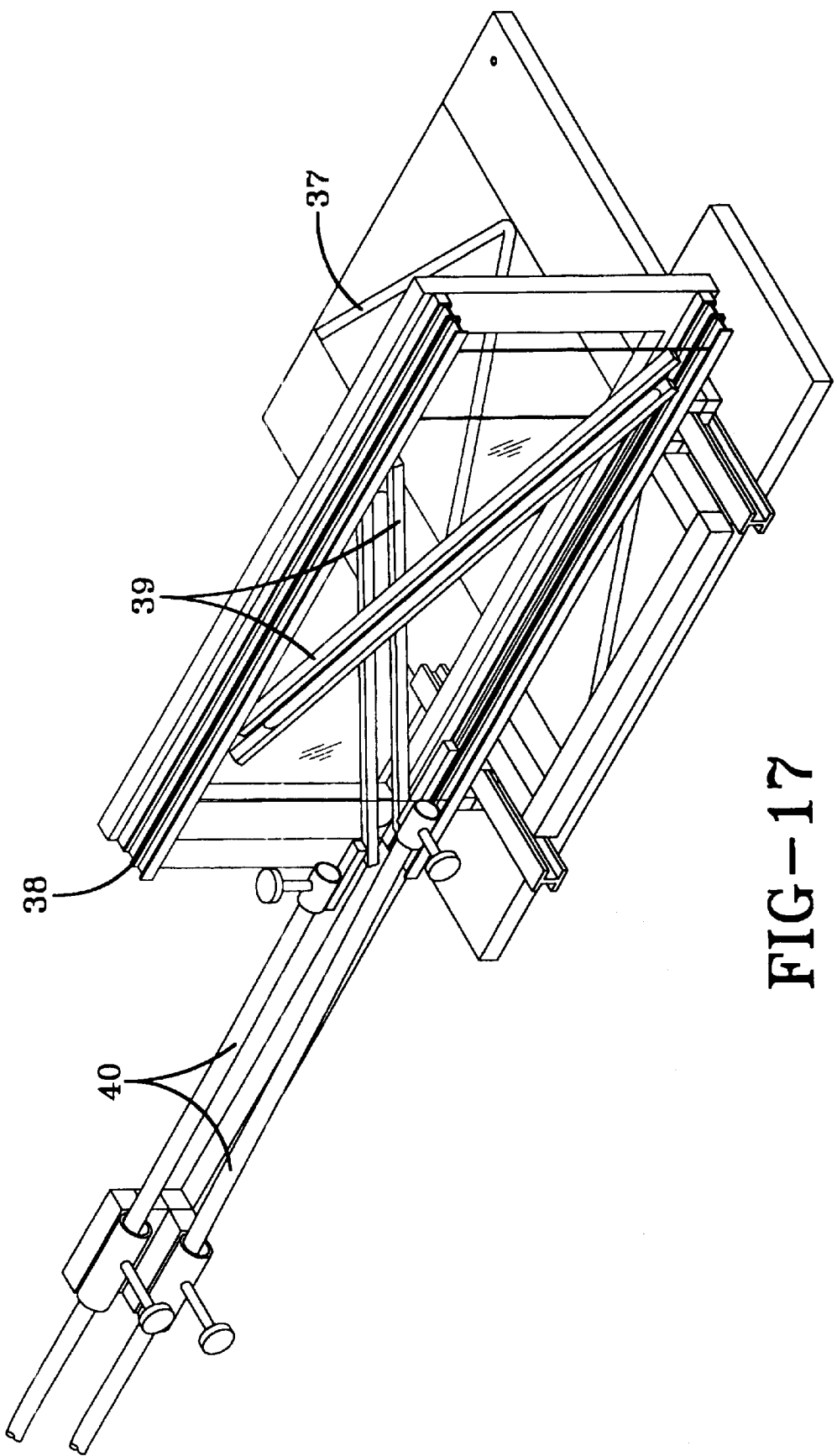
FIG. 17 is a perspective view of another stereotactic device that may be used in accordance with one embodiment of the present invention.

FIG. 17 shows the assembled device components. There are preferably five main components: a bottom rotation support plate (not shown), a base rotating "W" base pattern 37, a flat plate breast compressor 38, two sliding oblique "X" pattern pairs and needle support system 39, and remote control cables 40, along with several optional breast compression sponges (not shown).

In a preferred embodiment, a base plate fits into the spaces between the column supports of the surface coil. There is a small rod protruding from the bottom rotation support plate that acts as an axis point that the remaining device rotates around as a unit so that it can be precisely aligned with the axial section plane. A remote-control cable is fixed to the bottom support plate and the rotating "W" base pattern.

The rotating base of the device preferably has a dual-angle pattern (Chakeres pattern "W") that is below the breast. The pattern may be constructed of small tubes filled with image-conspicuous KY jelly or other image-conspicuous material as a sterile contrast agent. These tubes may be visible on both T1 and T2-weighted images. This pattern may be used to align the device with the axial plain.

There is preferably a vertical clear diaphragm compression plate that pushes the breast towards the center of the coil. A soft plastic sponge may be placed on the medial side of the breast that conforms to the breast's shape and size to help maintain its position comfortably while compressed. This compression plate preferably slides horizontally over the "W" pattern.

The needle may be held at the intersection point of two crossing diagonals forming an "X" shaped pattern. Each diagonal pattern may be made of two image conspicuous tubes with a space between for the needle. The diagonals are preferably adjacent to each other and slide past each other just outside of the compression plate. These diagonals of the "sliding X" may be constructed of two tubes each filled with image-conspicuous material. At the intersection of the "X" there is preferably a needle support system that holds the needle precisely parallel to the base and parallel to the image plane.

The combination of the base plate "W" and the sliding "X" patterns may control the needle path so that its vector is parallel to a flat base surface of the pattern and parallel to a perpendicular line crossing the base patterns. Both may be aligned at the same dimension on the pattern. This relationship allows for millimeter accuracy of the needle placement.

Hand manipulated cable remote controls with mm scales may allow 1-mm accuracy of the sliding "X" pattern needle support system without moving the table or patient, dramatically decreasing exam time.

The sliding "X" preferably defines the location of the needle in relationship to the image plane to a degree that is equivalent to the image resolution accuracy of the scanner, despite the fact that the needle itself cannot be seen.

Figure 18:
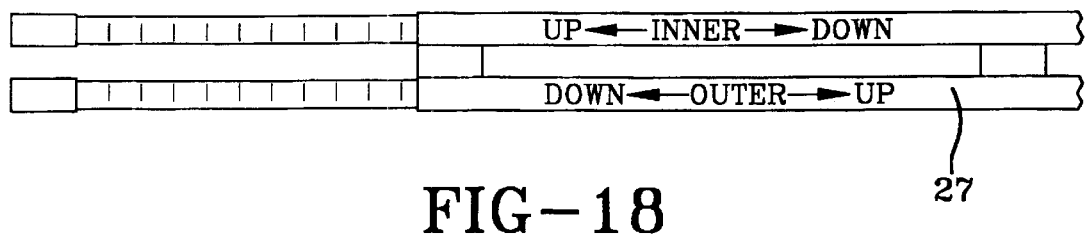
FIG. 18 is a side view of a remote-control handle that may be used in accordance with one embodiment of the present invention.

FIG. 18 shows a preferred remote-control handle. Each sliding diagonal plate preferably has its own calibrated-control remote cable that is clearly labeled on the handle. With this design and in this case, every 10 mm of movement of the handle can change the vertical position of the "X" plates by 5 mm.

Figure 19:
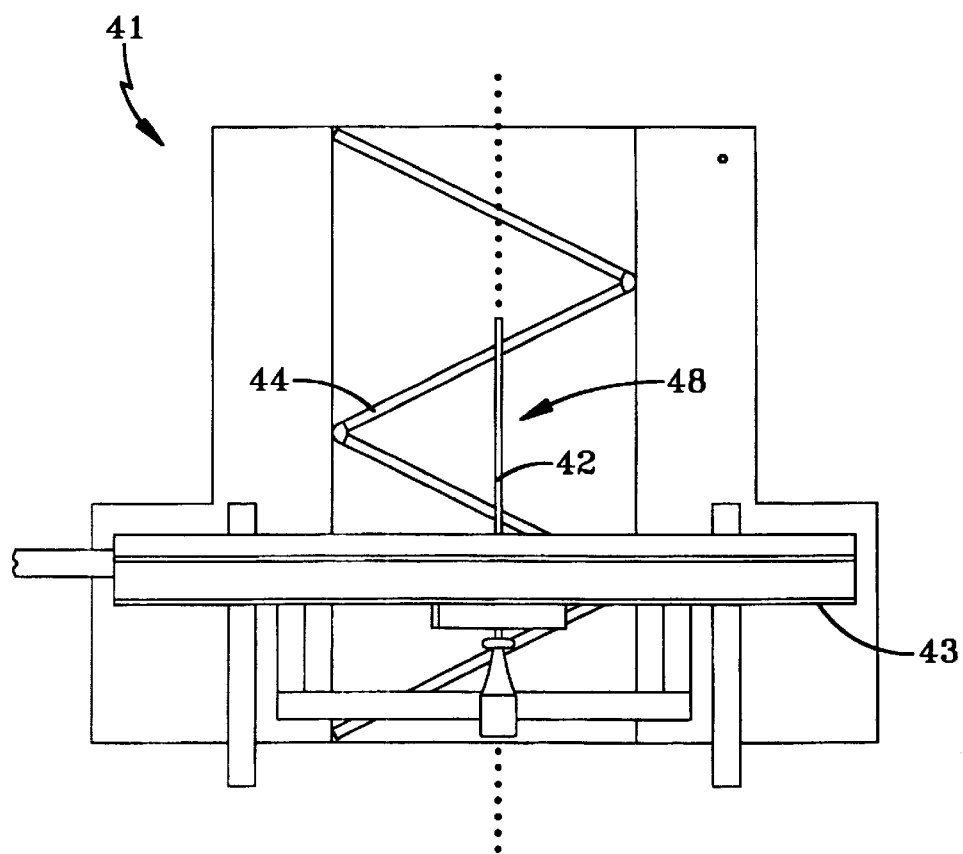
FIG. 19 is a top view of a stereotactic device that may be used in accordance with one embodiment of the present invention.

FIG. 19 shows a preferred stereotactic device 41 looking from superior to inferior (top down). The needle 42 here is held perpendicular to the compression plate 43 and "parallel" to the base "W" pattern 44. The correct alignment of the "W" pattern to the image plane insures the accuracy of the needle placement.

Figure 20:
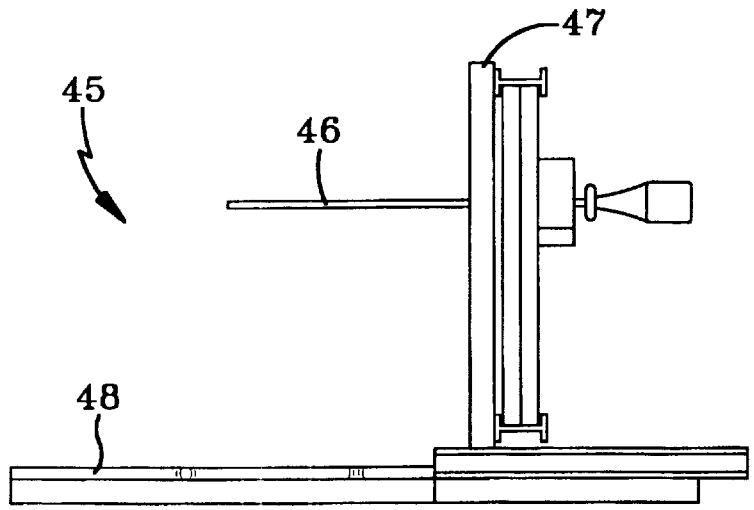
FIG. 20 is a side view of a stereotactic device that may be used in accordance with one embodiment of the present invention.

FIG. 20 shows a view of the device 45 parallel to a table. The needle 46 is held perpendicular to the compression plate 47, and parallel to the base "W" pattern 48. This ensures the accurate positioning of the needle despite the fact that the needle is not visible on MR unless it is in the patient.

Figure 21:
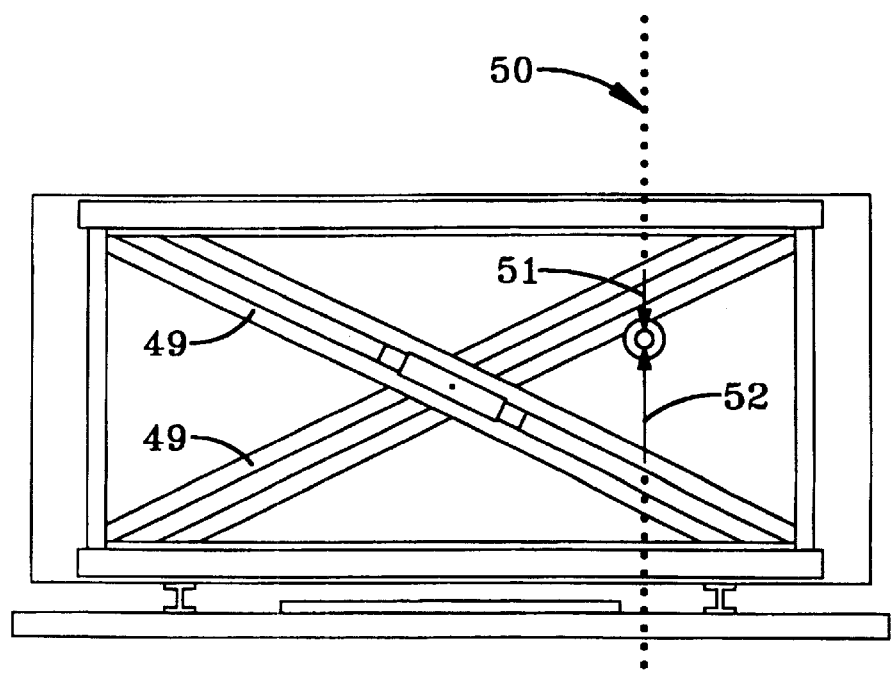
FIG. 21 is a front view of a stereotactic device that may be used in accordance with one embodiment of the present invention.

FIG. 21 is a side view of the device showing how any point within the breast compression plate region can be targeted using the two opposite diagonal sloping patterns 49. The lateral or horizontal translation of the patterns may be converted into adjustments in both the X and Y dimensions. The only dimension that the operator may need to be concerned with here is the vertical dimension, which is parallel to the axial image plane 50 (dotted line). The distance (in mms) from the midpoint between the two limbs of one sloping diagonal pattern to the target may be measured on the image and then actuated with the remote-control handle.

In this example the target is a circle. The distance from the inner pattern to the target 51 is shown and the distance from the outer pattern to the target 52 is shown.

Figure 22:
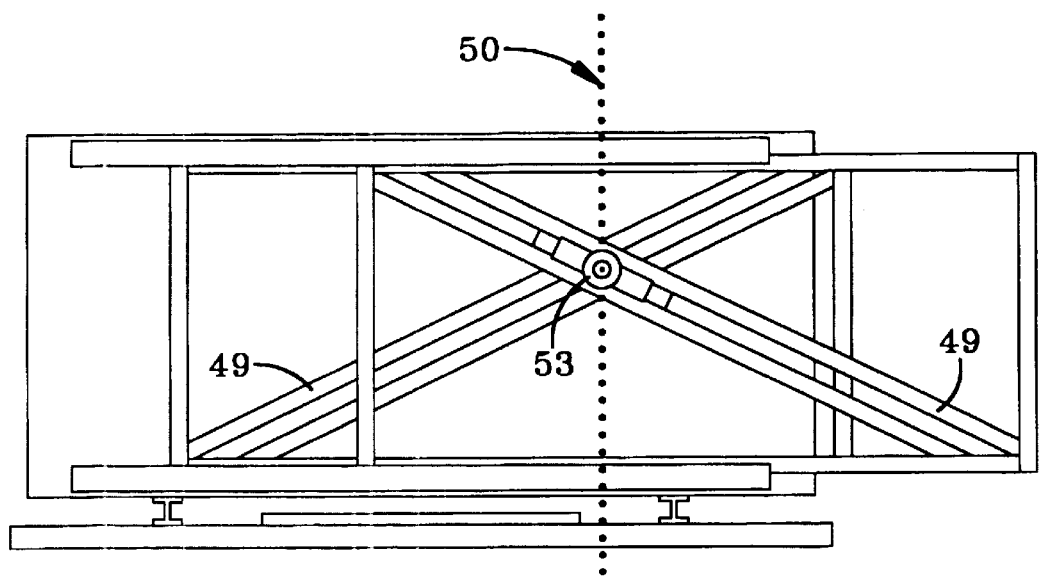
FIG. 22 is front view of a stereotactic device after adjustment that may be used in accordance with one embodiment of the present invention.

FIG. 22 shows the position of the patterns after these remote-controlled adjustments. This figure demonstrates that the needle at the center of the "X" is preferably centered on the chosen target location 53 after only one remote-control adjustment. If the alignment is not ideal, minor adjustments can be made after each image.

A breast phantom, which may contain multiple small targets of varying sizes imitating masses, may be placed on the surface coil in a position that mimickss imaging a patient in an axial position (with the breast being compressed from the lateral side by the compression-stereotactic plate). This allows breast compression without interference to precise needle placement. The compression plate may be covered in clear plastic that can be perforated by the needle.

Utilizing the device, a series of tests was completed to demonstrate the three-dimensional spatial accuracy, versatility and speed of needle placement into small targets. The needle and vector support were positioned accurately to within 2–3 mm of the chosen target by remote-control within a few minutes. Following positioning of the needle adjacent the target, the whole device was moved out of the scanner to advance the needle the final measured distance to the target site. Final confirmation images were acquired to verify the accurate placement of the probe.

Figure 23:
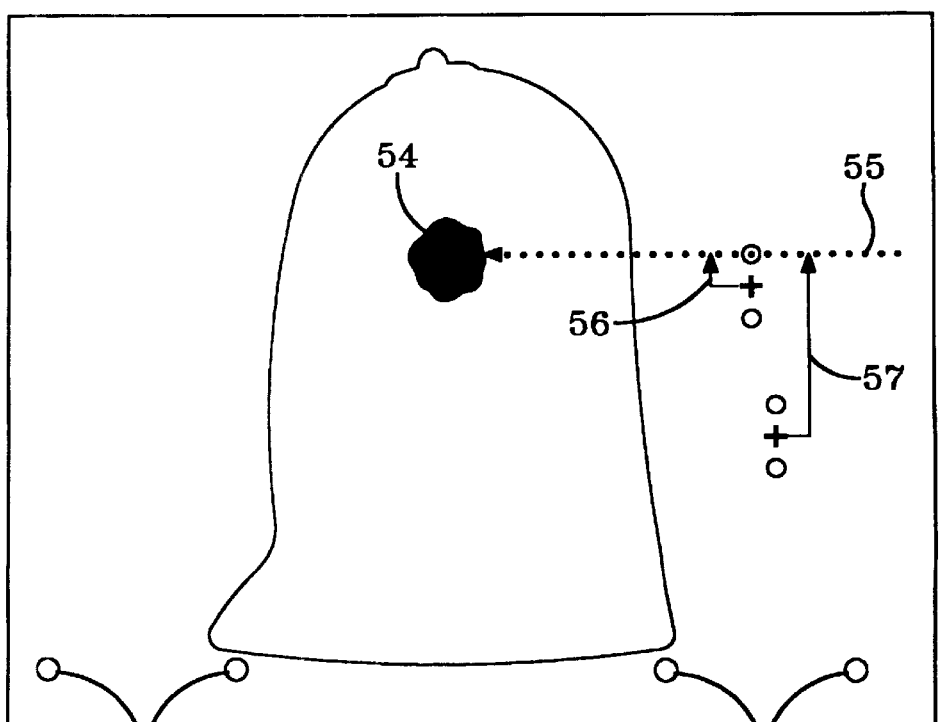
FIG. 23 shows an axial localizing image of a breast phantom that may be used in accordance with one embodiment of the present invention.

The device was placed in the breast coil on the MR table and an axial localizing image series was obtained, first shown in FIG. 23. A General Electric 1.5 Tesla Horizon system was used for all of the imaging. Fast spin-echo TR 400, TE 15 images were acquired. The FOV was 24 cm, and the matrix was 256 by 256 pixels. The slice thickness was 2 mm and they were contiguous. Four images were usually acquired with one acquisition. The initial image time was 56 seconds. All mm distance measurements were made directly from the scanner console using a mouse and standard hardware.

The first step required alignment of the base "W" pattern to the axial section plane. The complete device assembly (surface coil, phantom and device) was placed on the MR table and aligned using the MR light localizer so that it was visually parallel to the axial plane. A series of images were acquired to confirm parallel orientation. Measurements were made of the distances between the two limbs of the base "W" pattern. If the measured distances were not identical (which would indicate that the device was not parallel to the image plane), then the device was rotated about a fixed axis point the calibrated "degrees" equal to the difference in the distance between the two limbs of each base pattern. This was done using the remote-control cable and calibrated handle. Another image was acquired to confirm that the device and pattern were parallel to the image plane.

The second step was to identify the target and align the needle. A target was chosen in the breast phantom. The targets were seen as low signal structures within the phantom that varied in size and location. FIG. 23 shows an axial image through the breast phantom target 54 and device. The breast compression plate is not visible, but the phantom is compressed from the right in the figure. Note that the distances between the base "W" pattern "V"s 48 are identical, confirming that the "W" pattern is parallel to the image plane. This relationship also defines the needle vector, which will be parallel to this plane.

The dotted arrow 55 defines the ideal vector direction to the target. The distances from the midpoints of the inner 56 and outer 57 sliding diagonal "X" patterns are shown as vertical arrows. These distances may be actuated using the remote-control handle.

Figure 24:
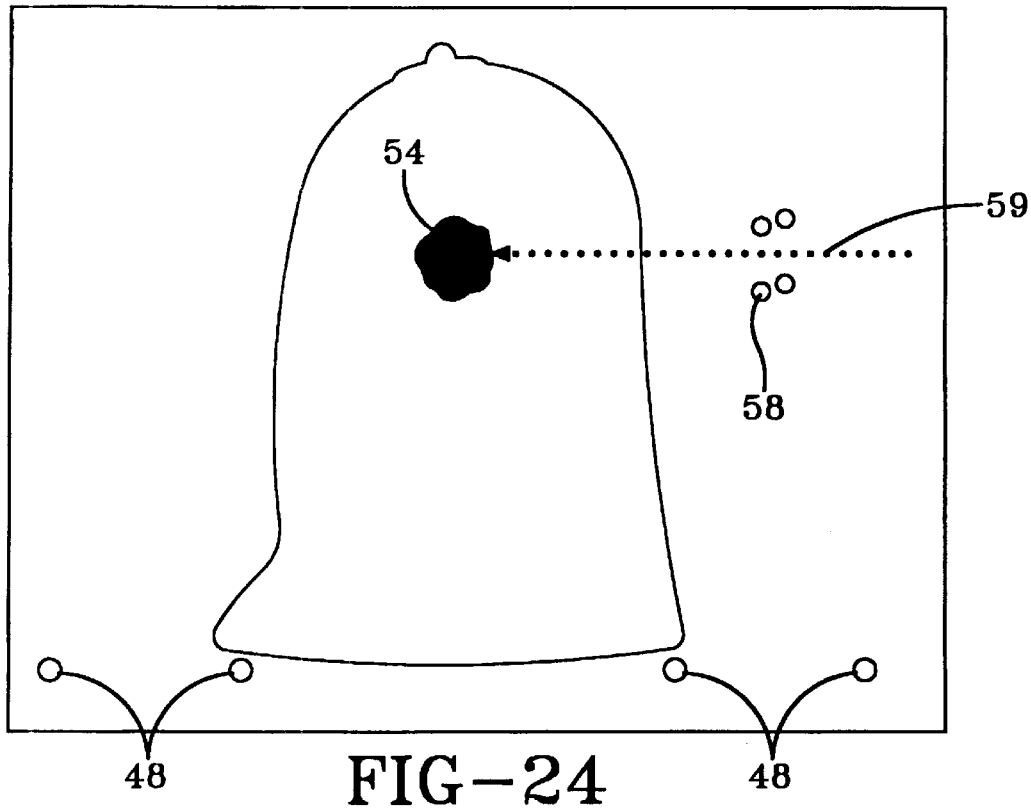
FIG. 24 shows another axial localizing image of a breast phantom that may be used in accordance with one embodiment of the present invention.

The third step was to align the sliding "X" patterns with the target. FIG. 24 shows a follow-up image, again identifying the location of the sliding "X" patterns and the needle. In this case the inner "X" pattern 58 is not precisely centered on the target vector 59 and it will be adjusted a few mms superiorly to match the target vector. Again, note that the needle is not visible, but its location is precisely defined to the mm by the location of the sliding patterns.

Figure 25:
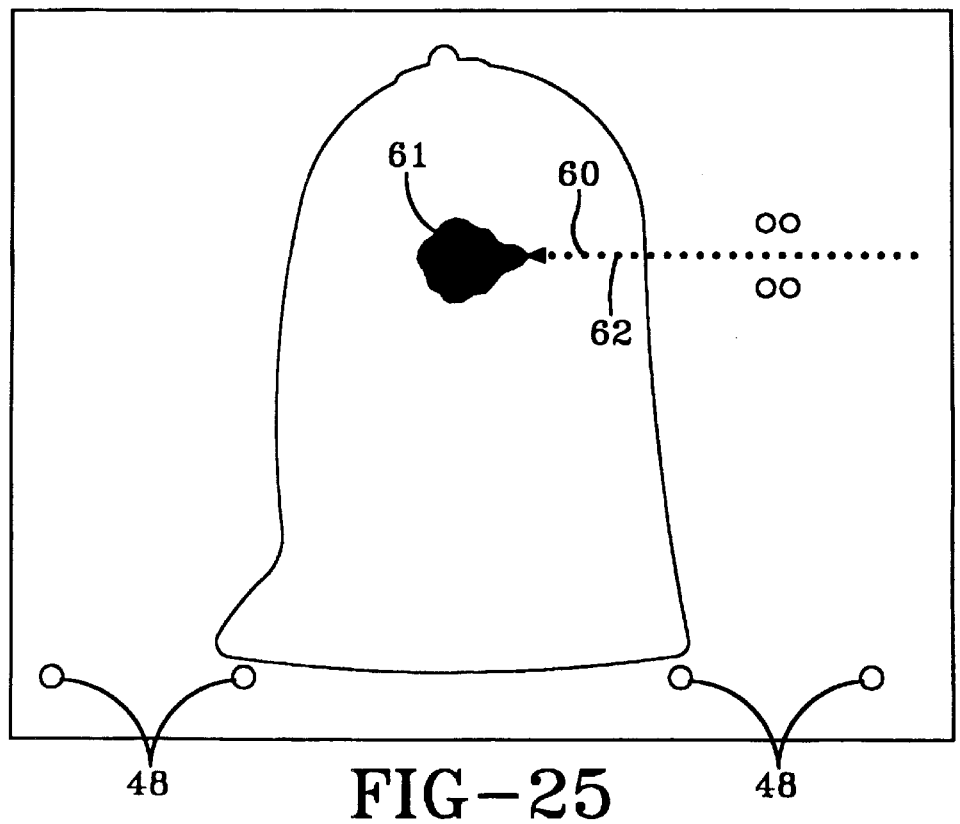
FIG. 25 shows another axial localizing image of a breast phantom that may be used in accordance with one embodiment of the present invention.
Figure 26:
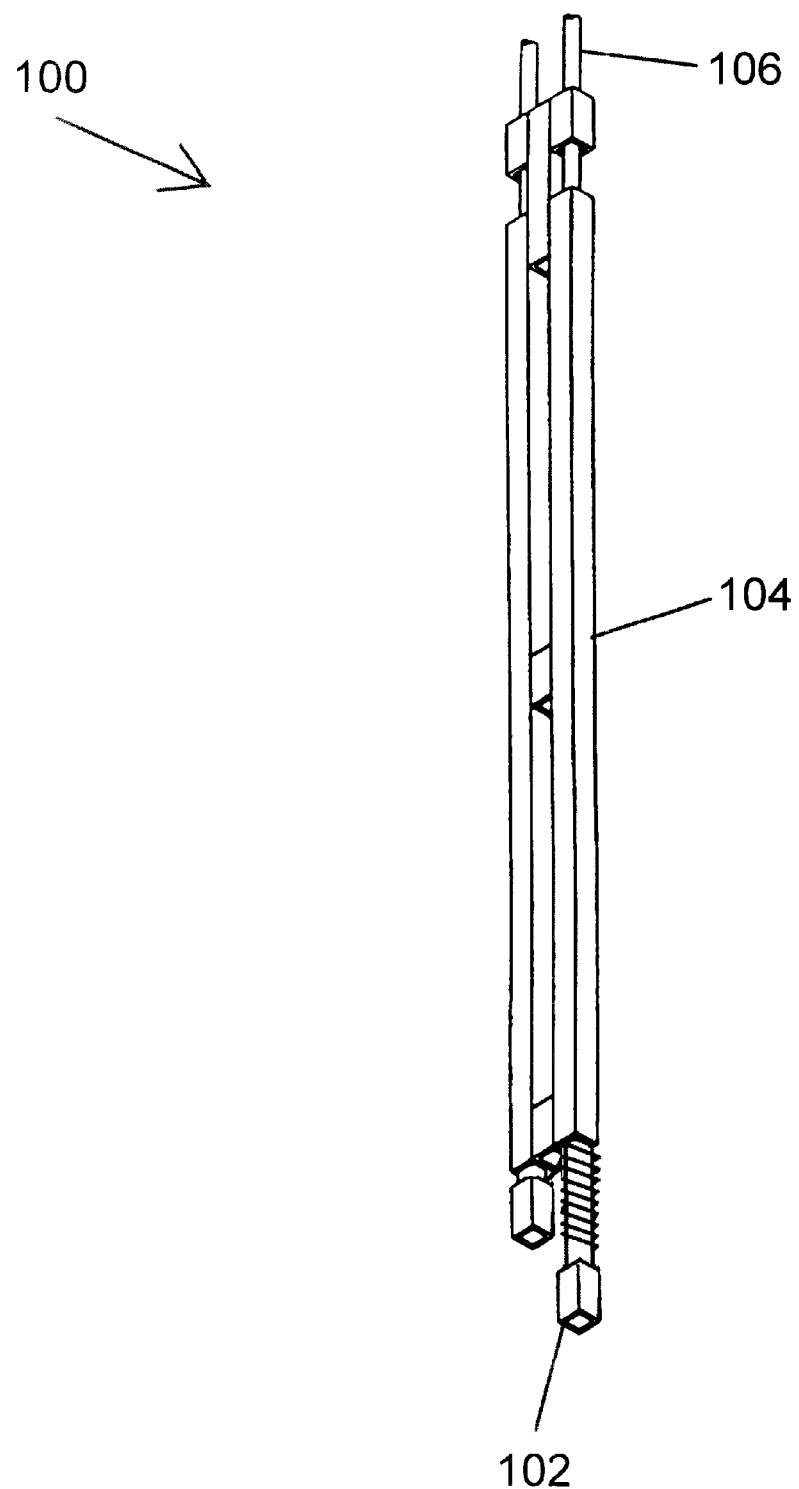
FIG. 26 shows a remote actuator that may be used in accordance with one embodiment of the present invention.

The fourth step was to place the needle into the target. FIG. 25 shows the needle 60 being advanced the measured number of mms into the target 61 using local anesthetic and an image is obtained to confirm its position. A biopsy or interventional procedure was then completed. Note that the desired vector 62 (dotted arrow) and the actual needle 60 position (black image defect) are very close after only a single pass along the vector defined by the patterns.

The device is preferably designed so that the sliding "X" and the breast compression plate can be removed, leaving only the needle in the patient if the operator desires device removal from his operational field.

Using this MRI-compatible device for placement of a needle within a target, we placed a probe in a breast phantom target with a confirmed accuracy of a few millimeters in three dimensions within a few minutes of first identifying the target on the initial scan. Remote-control capability saved valuable time in setting up the procedure.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

REFERENCES

1. Orel S, Schnall M, Powell M, et al, Staging of suspected breast cancer: effect of MR imaging and MR- guided biopsy, Radiology 1995;196:115–122
2. Stelling C, Breast cancer staging with contrast material-enhanced MR imaging: should it change patient treatment?, Radiology 1995;196:16–18
3. Mumtaz H, Hall-Craggs M, Wotherspoon A, Laser therapy of breast cancer: MR imaging and histopathologic correlation, Radiology 1996;200:651–658
4. Orel S, Schnall M, Newman R, MR imaging-guided localization and biopsy of breast lesions: initial experience. Radiology 1994;193:97–102

What is claimed is:

1. A stereotactic device comprising:
   (i) a lower plane portion defining a lower plane, said lower plane portion comprising at least one pair of angled members of an imager-conspicuous material, each of said at least one pair of angled members defining an angle; and
   (ii) an upper plane portion defining a plane orthogonal to and above said lower plane portion, said upper portion comprising:
      (1) a framing structure;
      (2) a first and second plate comprising an imager-inconspicuous material, said first and second plate adapted to slide back and forth in a horizontal motion in said framing structure along said lower plane portion, said first and second plate each comprising a pair of parallel imager-conspicuous members, said pairs of parallel imager-conspicuous members aligned on said plates so as to intersect one another forming an intersection, said pairs of parallel imager-conspicuous members aligned on said plates such that said intersection of one of said imager-conspicuous members on said first plate with one of said imager-conspicuous members on said second plate forms an angle, said first and second plates having an open passage extending therethrough and at the intersection between said pairs of parallel imager-conspicuous members through which at least portions of a probe may be passed.

2. A stereotactic device according to claim 1 additionally comprising a probe alignment structure comprising an imager-inconspicuous material, said alignment structure located at said open passage extending through said first and second plates, said alignment structure adapted to move and reside within said open passage as a result of movement of at least one of said first and second plates, said alignment structure comprising an opening through which at least portions of a probe may be passed.

3. A stereotactic device according to claim 1 wherein said intersection has a vertical position and wherein said framing structure additionally comprises a graduated position scale to accord said vertical position of said intersection of said image conspicuous members to said horizontal movement of a said plate.

4. A stereotactic device according to claim 1, said device additionally comprising at least one remote actuator to move said first and second plates with respect to one another.

5. A stereotactic device according to claim 4, wherein said at least one remote actuator comprises a device to measure its movement, said device comprising:
   (a) a hollow outer sleeve;
   (b) a threaded member having threads, said threaded member adapted to move within said sleeve, said threads having a distance between adjacent said threads; and
   (c) an engaging member extending into said hollow outer sleeve a sufficient distance to engage said threads of said threaded member so as to permit said threaded member to be moved within said hollow outer sleeve by a turning motion of said threaded member, and said engaging member disposed with respect to said threaded member so as to permit said threaded member to be moved discrete distances approximately equal to said distance between adjacent said threads within said hollow outer sleeve by direct pushing or pulling motion so as to overcome the engagement of said engaging member and said threads.

6. A stereotactic device according to claim 1 wherein said lower portion additionally comprises a rotation attachment adapted to allow said lower portion to rotate with respect to a flat surface.

7. A stereotactic device according to claim 1 wherein each of said first and second plates further comprises a graduated linear distance position scale.

8. A stereotactic device according to claim 1 wherein said members comprising an imager-conspicuous material are selected from the group consisting of metal members, hollow polymeric members filled with an imager-conspicuous material, and polymeric members treated with an imager-conspicuous material.

9. A stereotactic device according to claim 1 wherein each of said pairs of imager-conspicuous members is separated by a different distance.

10. A stereotactic device according to claim 1 additionally comprising a planar compression member, said planar compression member positioned in said framing structure so as to prevent said first and second plates from contacting a target surface.

11. A stereotactic device according to claim 10 wherein said planar compression member is selected from the group of image inconspicuous members consisting of perforable sheets, meshes, or sliding rigid plates.

12. A breast biopsy system for supporting an upper torso of a female and for performing a biopsy on a breast of said female comprising:
   (i) a stereotactic device, said stereotactic device comprising a base portion attached to:
      (a) a lower plane portion defining a lower plane, said lower plane portion comprising at least one pair of angled members of an imager conspicuous material, each of said at least one pair of angled members defining an angle; and (b) an upper plane portion defining a plane orthogonal to and above said lower plane portion, said upper portion comprising:

(1) a framing structure;

(2) a first and second plate comprising an imager-inconspicuous material, said first and second plate adapted to slide back and forth in said framing structure along said lower plane portion, said first and second plate each comprising a pair of parallel imager-conspicuous members, said pairs of parallel imager-conspicuous members aligned on said plates so as to intersect one another forming an intersection, said pairs of parallel imager-conspicuous members aligned on said movable alignment structures such that said intersection of one of said imager-conspicuous members on said first movable alignment structure with one of said imager-conspicuous members on said second movable alignment structure forms an angle, said first and second plates having an open passage extending therethrough and at said intersection between said pairs of parallel imager-conspicuous members through which at least portions of a probe may be passed; and (3) an alignment structure comprising an imager-inconspicuous material, said alignment structure located at said open passage extending through said first and second plates, said alignment structure adapted to move and reside within said open passage as a result of movement of at least one of said first and second plates, said alignment structure comprising an opening through which at least portions of a probe may be passed;

(ii) a positioning structure for supporting a female having an upper torso and positioning a breast of said female, said positioning structure comprising:

(a) a lower base portion, said lower base portion comprising at least one opening through which at least a portion of said breast may pass;

(b) an upper supportive portion, said upper supportive portion adapted to approximately conform to a said upper torso, said upper supportive portion comprising at least one opening through which at least a portion of said breast may pass; and (c) at least one supportive member connecting said upper supportive portion to said lower base portion, said at least one supportive member adapted to maintain a distance between said lower base portion and said upper supportive portion so as to allow passage of at least a portion of said stereotactic device; and (iii) at least on flexible supportive member for shaping and supporting said breast, said supportive member adapted to be moved and shaped according to the size and shape of said breast.

13. A breast biopsy system according to claim 12 wherein said flexible supportive member is selected from the group consisting of pillows, sponges, and foams.

14. A method for inserting a probe into subject tissue, said method comprising the steps of:

(a) placing said subject tissue into an imaging device;

(b) placing a stereotactic device next to said subject tissue, said stereotactic device comprising:

(1) a lower plane portion defining a lower plane, said lower plane portion comprising at least one pair of angled members of an imager-conspicuous material, each of said at least one pair of angled members defining an angle; and (2) an upper plane portion defining a plane orthogonal to and above said lower plane portion, said upper portion comprising:

(i) a framing structure;

(ii) a first and second plate comprising an imager-inconspicuous material, said first and second plate adapted to slide back and forth in said framing structure along said lower plane portion, said first and second plate each comprising a pair of parallel imager-conspicuous members, said pairs of parallel imager-conspicuous members aligned on said plates so as to intersect one another forming an intersection, said pairs of parallel imager-conspicuous members aligned on said plates such that said intersection of one of said imager-conspicuous members on said first plane with one of said imager-conspicuous members on said second plate forms an angle, said first and second plates having an open passage extending therethrough and at said intersection between said pairs of parallel imager-conspicuous members through which at least portions of a probe may be passed; and (iii) an alignment structure comprising an imager-inconspicuous material, said alignment structure located at said open passage extending through said first and second plates, said alignment structure adapted to move and reside within said open passage as a result of movement of at least one of said first and second plates, said alignment structure comprising an opening through which at least portions of a probe may be passed;

(c) acquiring an image of said subject tissue and said stereotactic device so as to locate a target point in said subject issue in the image plane, and so as to locate the intersect point of said imager-conspicuous members of said stereotactic device with the image plane;

(d) adjusting one or both of said first and second plates so as to place said intersection points even with the target point, so as to form a probe vector; and (e) inserting a probe along said probe vector to said target point.

15. A method for inserting a probe into subject tissue according to claim 14 additionally comprising the step of preparing said subject tissue for sterile handling and treatment using an appropriate surgical preparation procedure.

16. A method for inserting a probe into subject tissue according to claim 14 additionally comprising the step of placing a pillow or other supportive member in said imaging device to support said subject tissue.

17. A method for inserting a probe into subject tissue according to claim 14 additionally comprising the step of confirming the position of said probe in said target by imaging.

18. A method for inserting a probe into subject tissue according to claim 14 additionally comprising the step of removing a sample of said subject tissue.

19. A method for inserting a probe into subject tissue according to claim 14 additionally comprising the step of removing said probe and all said components.

20. A method for supporting an upper torso of a female having breasts and for performing a biopsy on a breast of said female containing a target interior, said method comprising the steps of:

(a) bringing a stereotactic device into imaging proximity with a magnetic resonance surface coil, said magnetic resonance surface coil having an upper supportive structure, said stereotactic device having plates, each said plate having a sliding pattern pair, each said sliding pattern pair having a midpoint;

(b) placing a supportive member on said magnetic resonance surface coil;

(c) placing said torso of a female upon said upper supportive structure of said magnetic resonance surface coil, allowing said breasts of said female to suspend from said upper supportive structure through appropriate circular openings, and supporting a said breast with said supportive member;

(d) bringing a stereotactic device into contact with a said breast;

(e) imaging said breast with an appropriate imaging device so as to form an image plane and locating a target in said breast;

(f) comparing said image plane of said imaging device to a base pattern of said stereotactic device;

(g) if said base pattern is not parallel to said image plane, rotating said stereotactic device to bring said stereotactic device parallel with said image plane;

(h) capturing another image to a computer screen so as to confirm said base pattern is parallel to said image plane;

(i) if parallel, drawing a vector on said computer screen towards said target and parallel to said base;

(j) measuring from said midpoint between each said sliding pattern pair to a chosen vector line so as to define a distance and direction that said sliding pattern pairs of said stereotactic device need to be moved;

(k) moving said plates of said stereotactic device to correct dimensions and in proper directions to confirm that a needle inserted in said stereotactic device is pointing at said target;

(l) confirming that said needle is in the correct vector position outside said female on a next image, and measuring the distance from said sliding pattern pairs to said target;

(m) confirming said needle position in said target by imaging;

(n) completing said biopsy, such as through removing tissue from said breast; and (o) removing said needle and all said components.

21. A stereotactic device comprising:

(a) a lower plane portion defining a lower plane, said lower plane portion comprising at least one pair of angled members of an imager-conspicuous material, each of said at least one pair of angled members defining an angle; and (b) an upper plane portion defining a plane orthogonal to and above said lower plane portion, said upper portion comprising:

(1) a framing structure; and (2) a first and second movable alignment structure comprising an imager-inconspicuous material, said first and second movable alignment structures adapted to slide back and forth in said framing structure along said lower plane portion, said first and second movable alignment structures each comprising a pair of parallel imager-conspicuous members, said pairs of parallel imager-conspicuous members aligned on said plates so as to intersect one another forming an intersection, said pairs of parallel imager-conspicuous members aligned on said movable alignment structures such that said intersection of one of said imager-conspicuous members on said first movable alignment structure with one of said imager-conspicuous members on said first movable alignment structure with one of said imager-conspicuous members on said second movable alignment structure forms an angle, said first and second movable alignment structures having an open passage extending there through and at the intersection between said pairs of parallel imager-conspicuous members through which at least portions of a probe may be passed.

22. A stereotactic device according to claim 21 additionally comprising a probe alignment structure comprising an imager-inconspicuous material, said probe alignment structure located at said open passage extending through said first and second movable alignment structures, said probe alignment structure adapted to move and reside within said open passage as a result of movement of at least one of said first and second movable alignment structures, said probe alignment structure comprising an opening through which at least portions of a probe may be passed.

* * * * *

UNITED STATES PATENT AND TRADEMARK OFFICE
CERTIFICATE OF CORRECTION

| | | |
|---|---|---|
| PATENT NO. | : 6,261,299 B1 | |
| APPLICATION NO. | : 09/449809 | |
| DATED | : July 17, 2001 | |
| INVENTOR(S) | : Donald W. Chakeres | |

Figure 1:
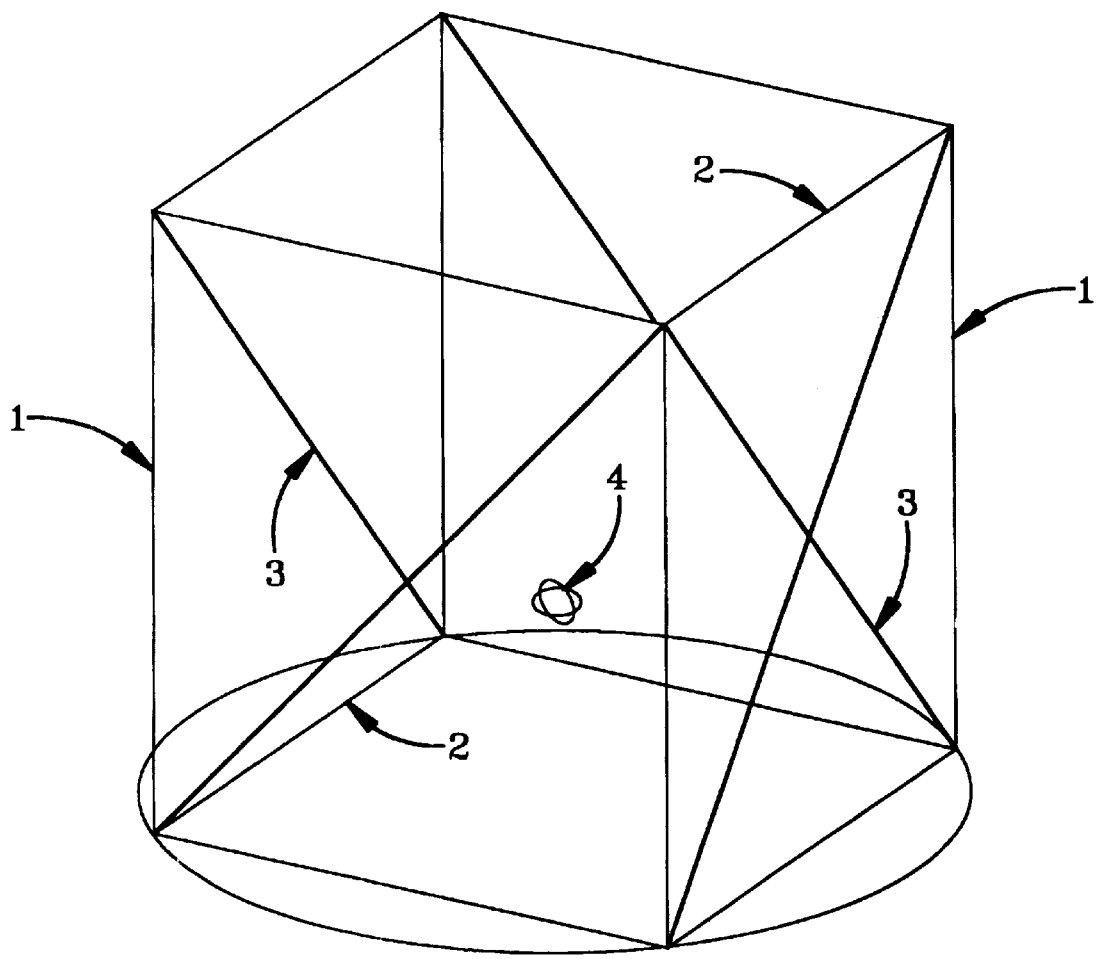
FIG. 1 is a schematic of an enveloping frame that is used for head stereotactic systems of the prior art.
Figure 2:
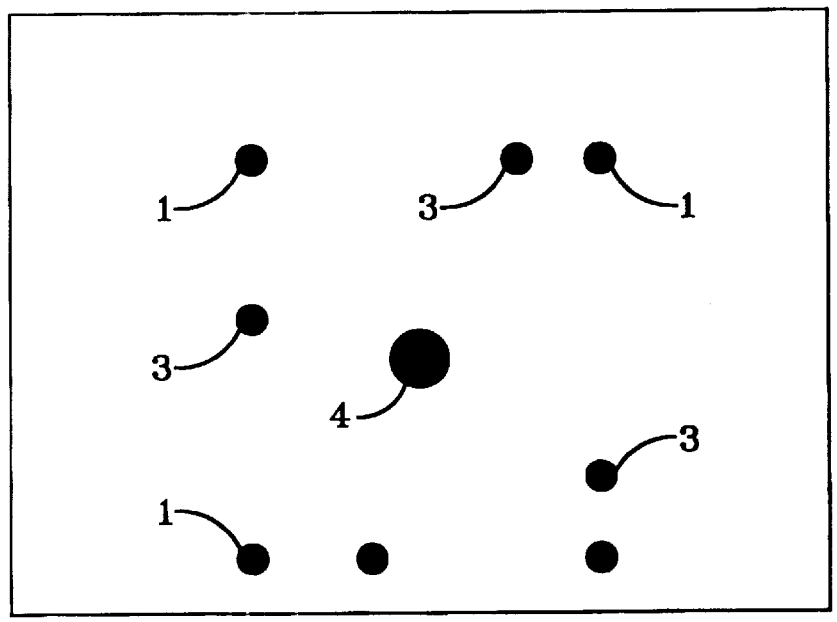
FIG. 2 is a schematic of an image obtained from a fixed frame rigid system in accordance with the prior art.
Figure 3:
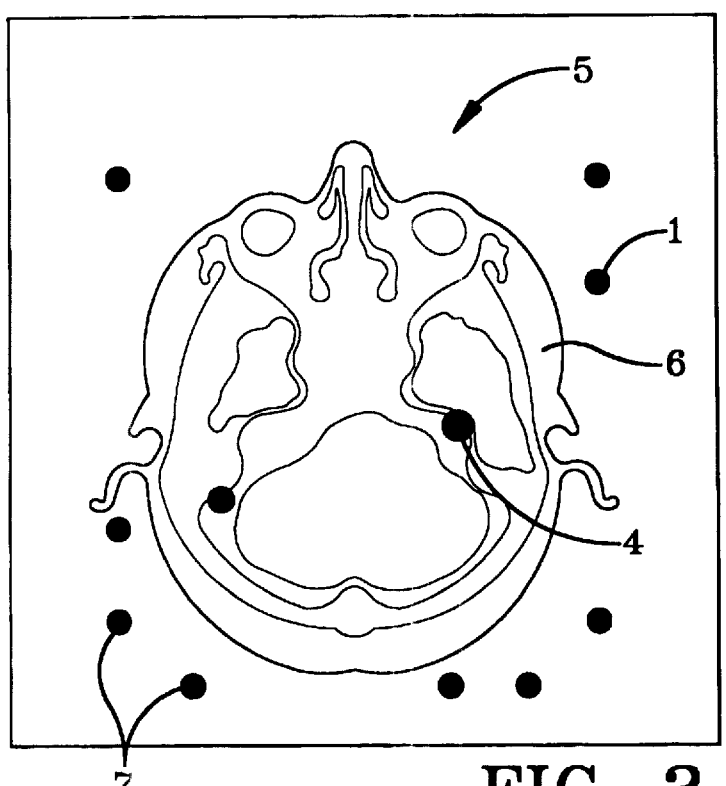
FIG. 3 shows an example of an MRI image showing the use of a fixed frame stereotactic unit used for head imaging in accordance with the prior art.
Figure 4:
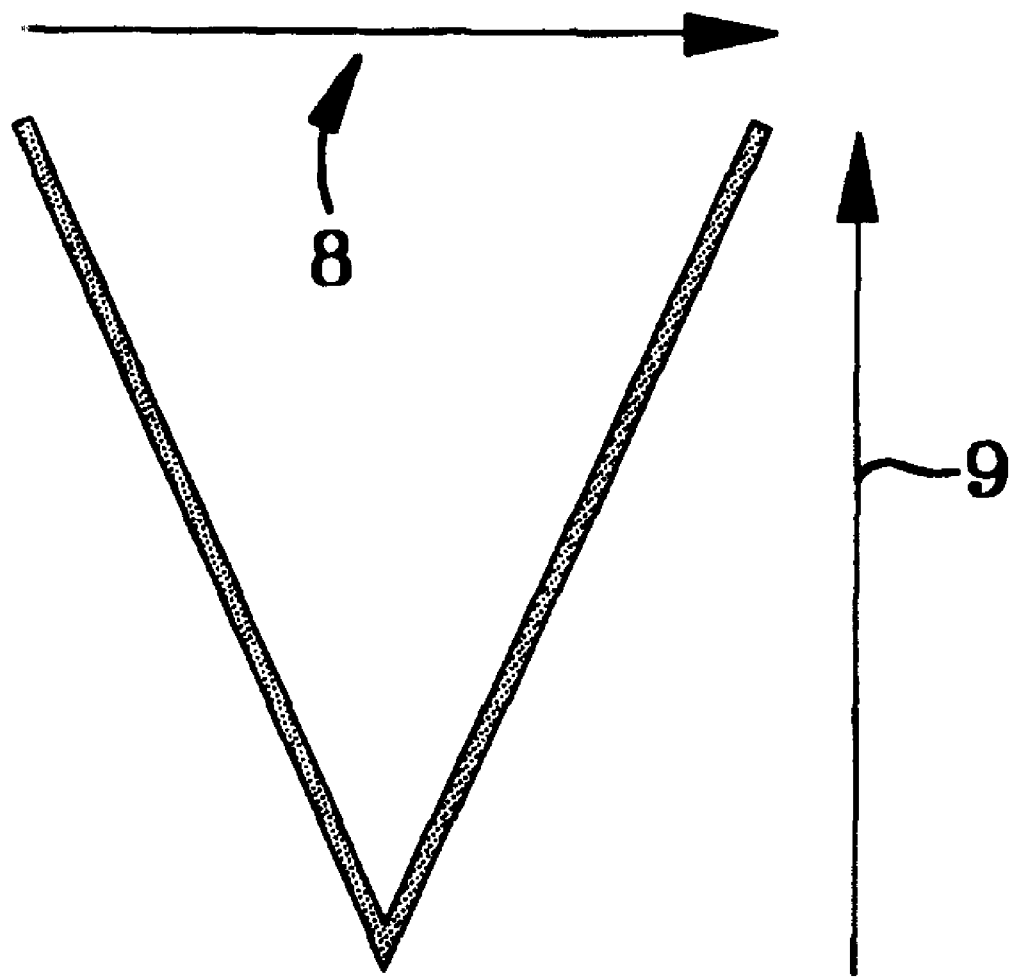
FIG. 4 shows an example of the stereotactic pattern generated by a device in accordance with the present invention.
Figure 5:
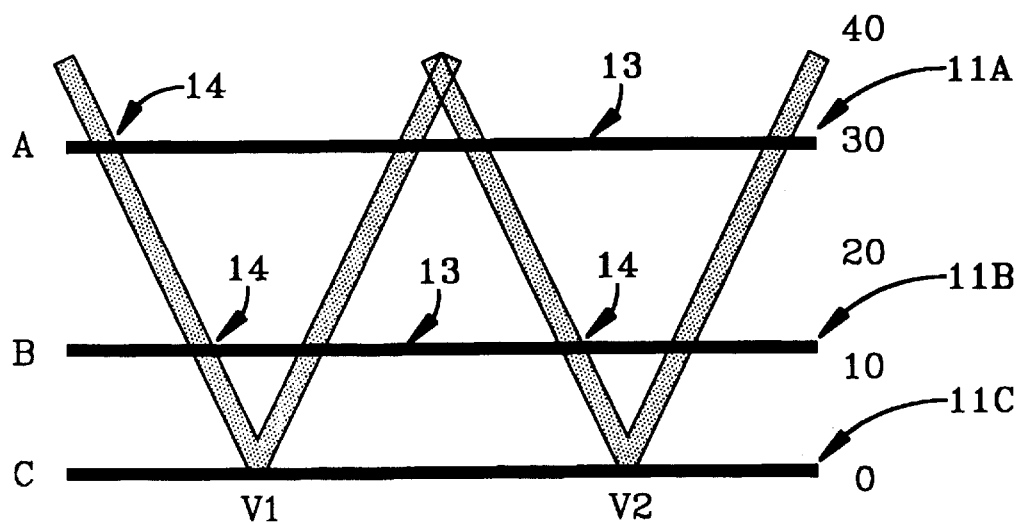
FIG. 5 shows a representation of two V-shaped patterns adjacent to each other, forming a "W"-like pattern, to illustrate the operation of a device in accordance with one embodiment of the present invention.
Figure 6:
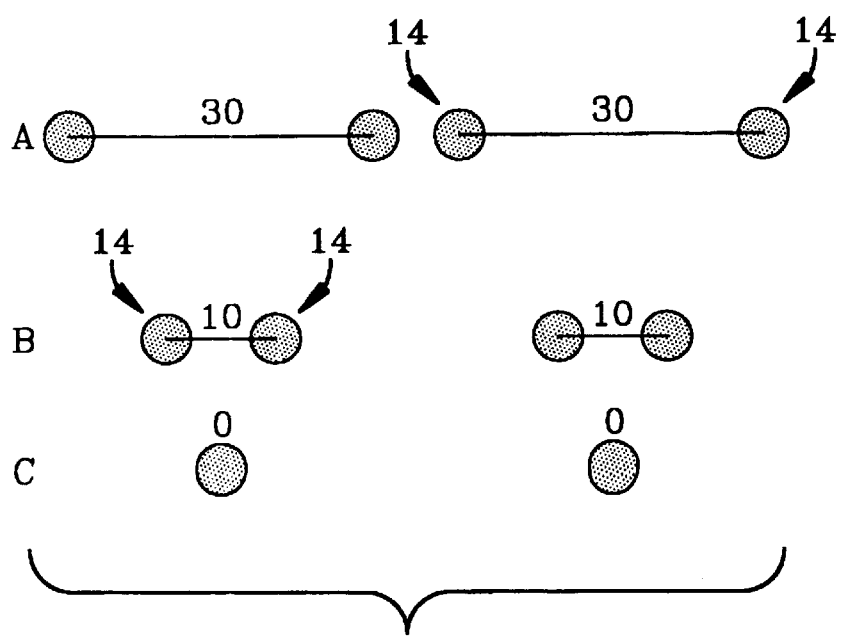
FIG. 6 is a view of the image perspective of each image slice representation shown in FIG. 5, to illustrate the operation of a device in accordance with one embodiment of the present invention.
Figure 6A:
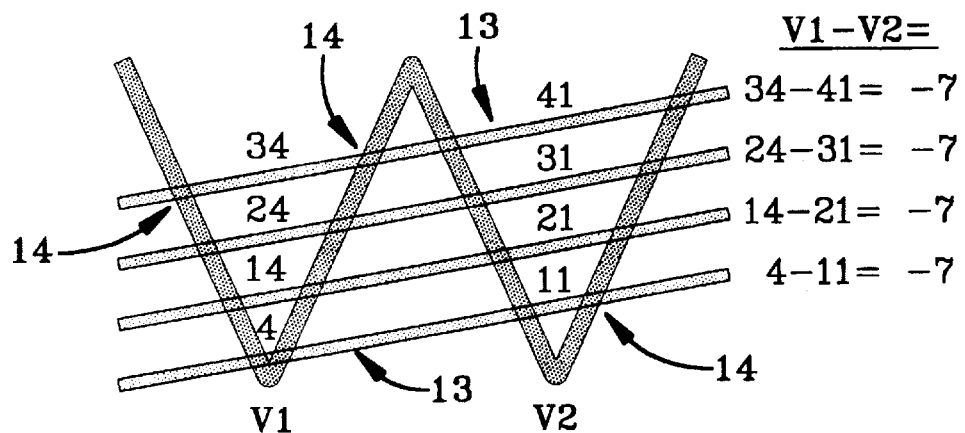
FIG. 6a is a view of the device-generated pattern, to illustrate the geometric basis of the operation of a device in accordance with one embodiment of the present invention.
Figure 6B:
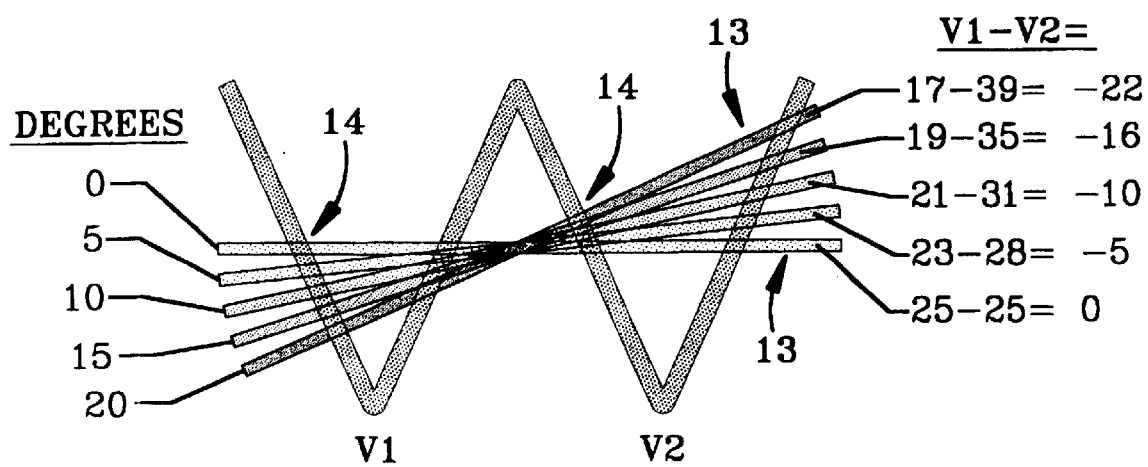
FIG. 6b is a view of the device-generated pattern, to illustrate the geometric basis of the operation of a device in accordance with one embodiment of the present invention.
Figure 7:
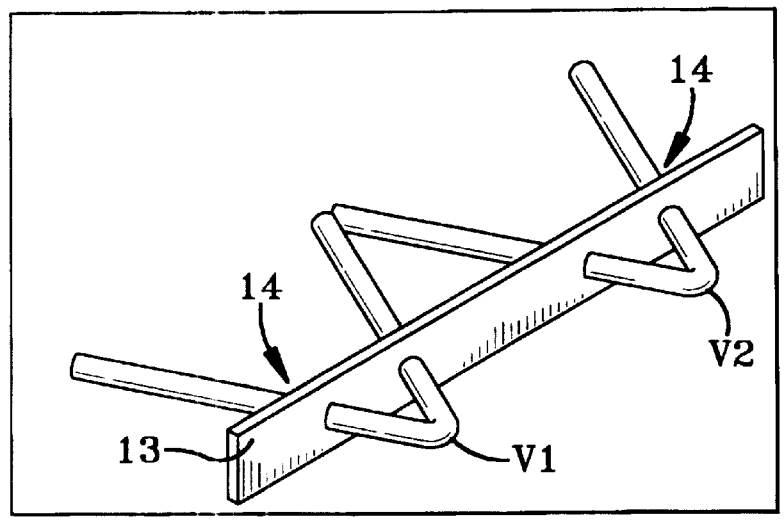
FIG. 7 is a cross-sectional view of the device-generated pattern, to illustrate the geometric basis of the operation of a device in accordance with one embodiment of the present invention.
Figure 7:
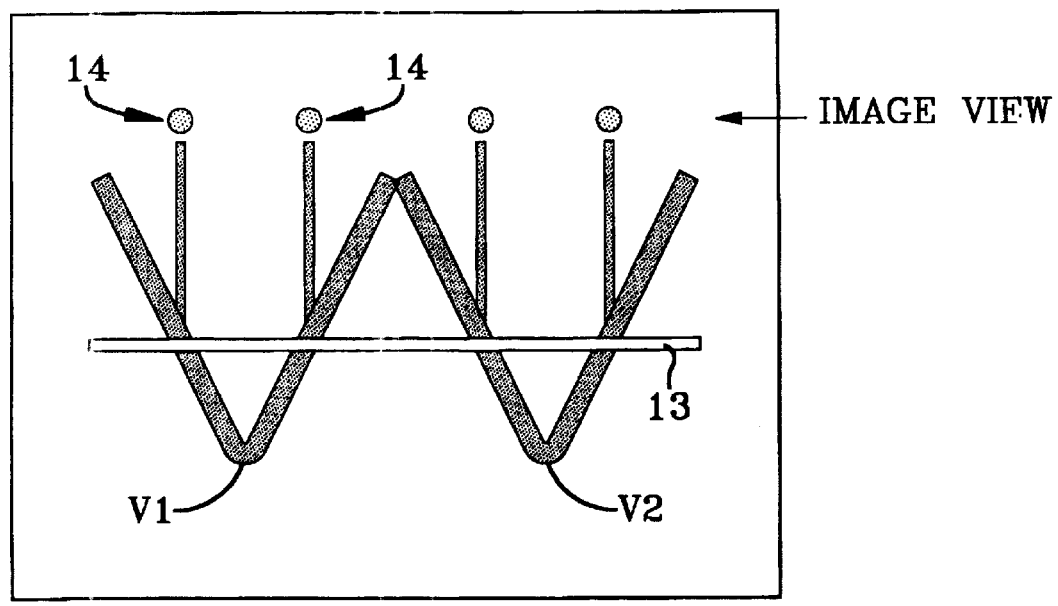
Figure 7A:
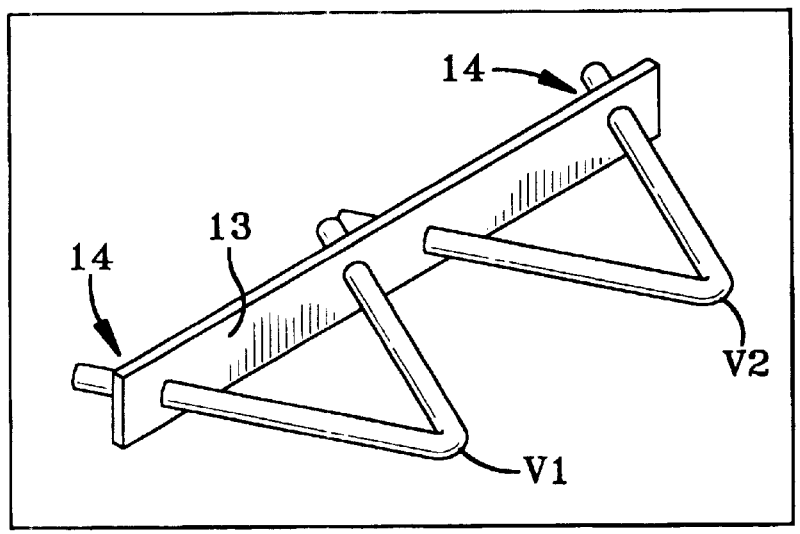
FIG. 7a is a cross-sectional view of the device-generated pattern, to illustrate the geometric basis of the operation of a device in accordance with one embodiment of the present invention.
Figure 7A:
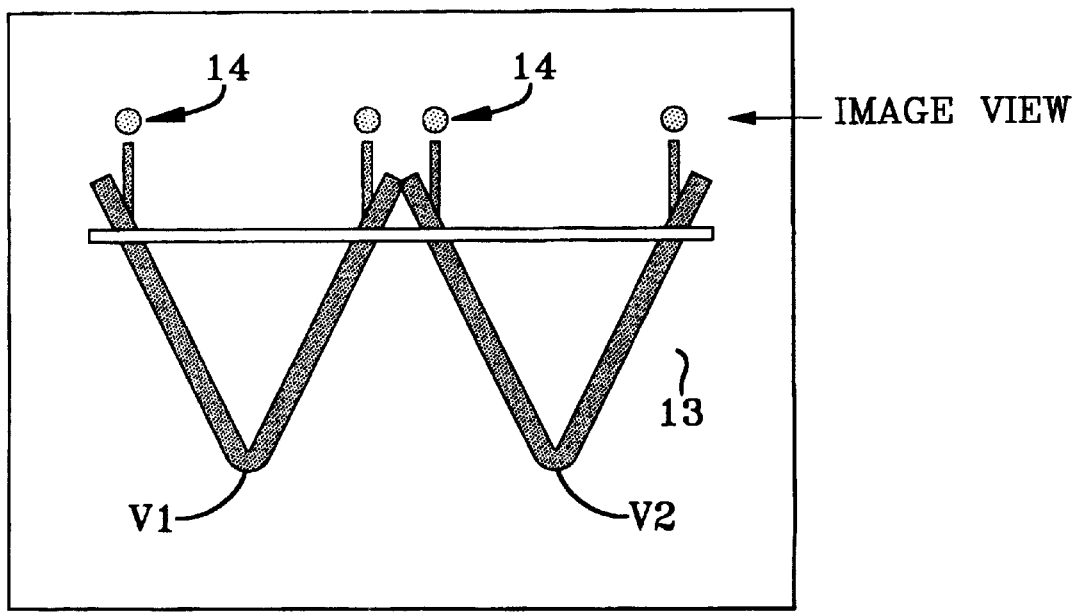
Figure 7B:
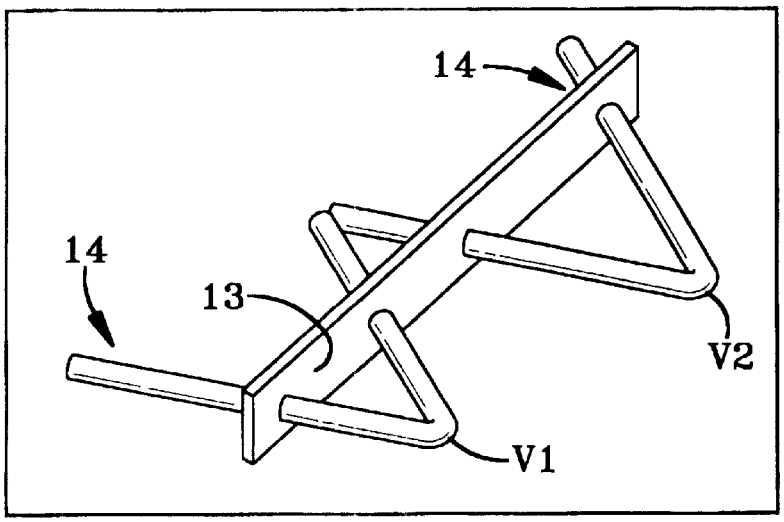
FIG. 7b is a cross-sectional view of the device-generated pattern, to illustrate the geometric basis of the operation of a device in accordance with one embodiment of the present invention.
Figure 7B:
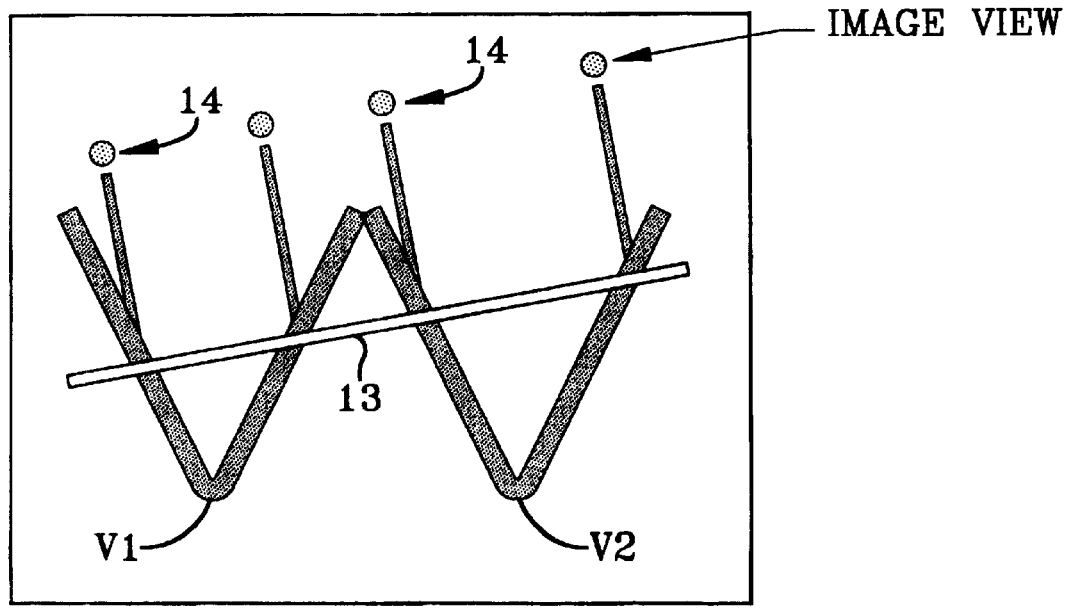
Figure 8:
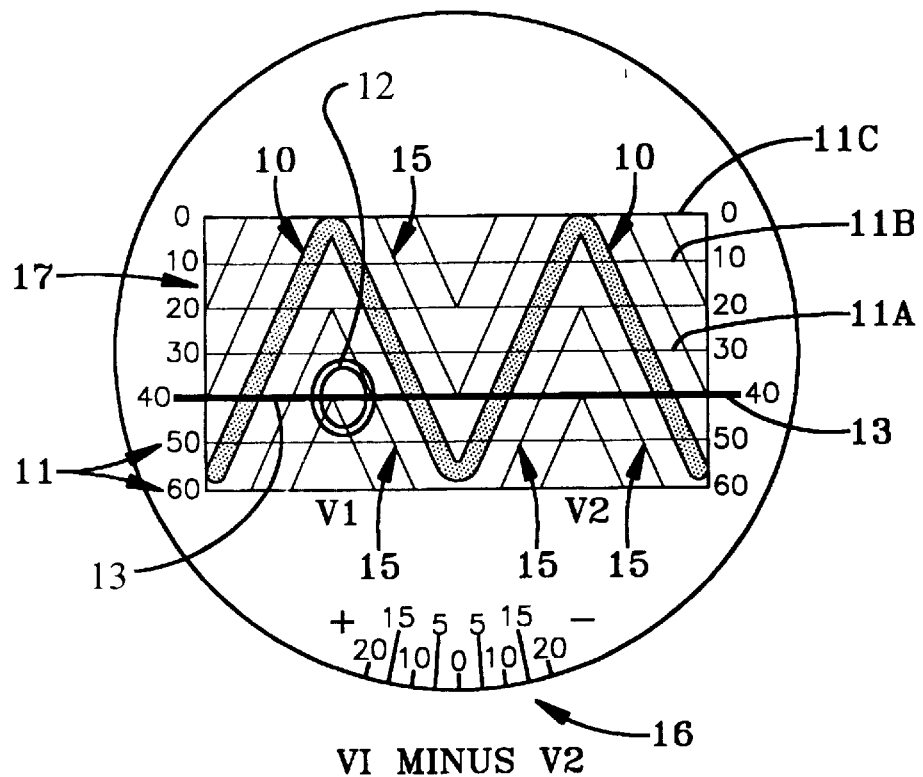
FIG. 8 is another view of the device-generated pattern, to illustrate the geometric basis of operation of a device in accordance with one embodiment of the present invention.
Figure 8A:
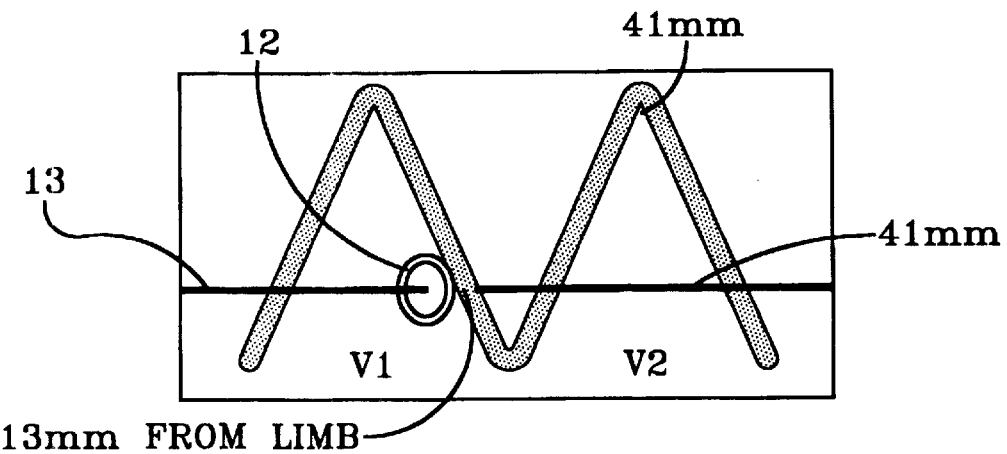
FIG. 8a shows CT and planar image views illustrating the geometric basis of operation of a device in accordance with one embodiment of the present invention.
Figure 9A:
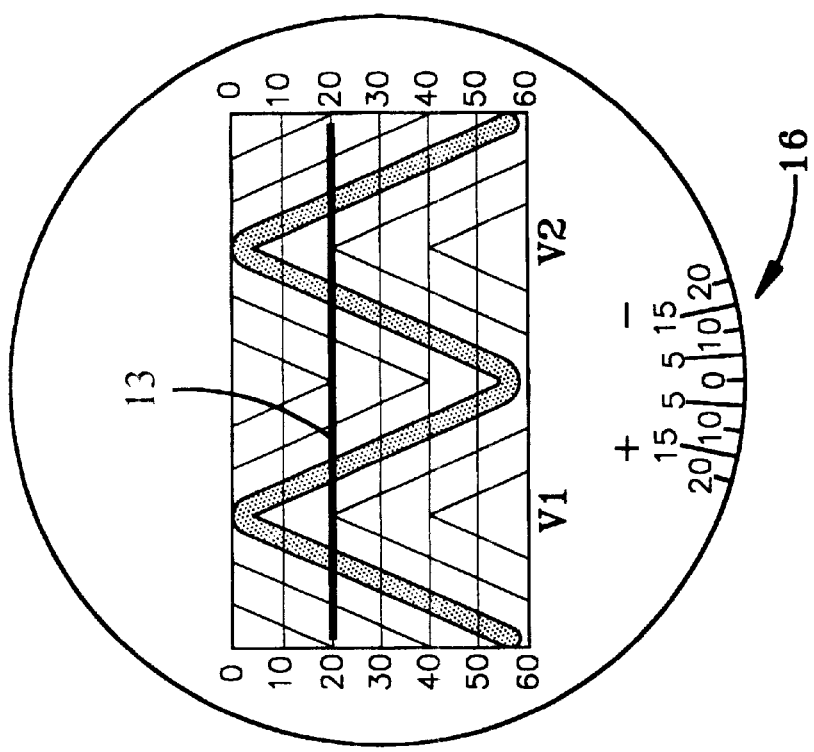
FIG. 9a is a view of the device-generated pattern, to illustrate the geometric basis of operation of a device in accordance with one embodiment of the present invention with regard to its rotation and alignment with the image plane—has been inserted after the paragraph that describes FIG. 9.
Figure 9:
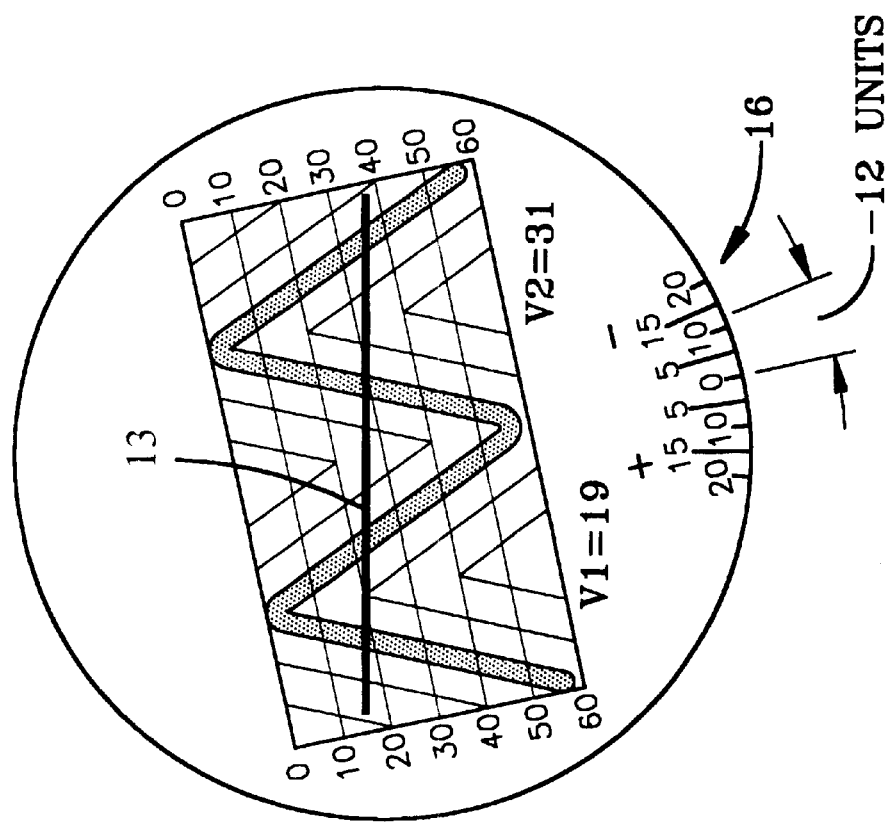
FIG. 9 is a view of the device-generated pattern, to illustrate the geometric basis of operation of a device in accordance with one embodiment of the present invention with regard to its rotation and to align with the image plane.

It is certified that error appears in the above-identified patent and that said Letters Patent is hereby corrected as shown below:

In column 8, line 64, please delete the words "—has been inserted after the paragraph that describes Fig. 7.";

In column 9, line 1, please delete the words "—has been inserted after the paragraph that describes Fig. 7a.";

In column 9, line 6, please delete the words "—has been inserted after the paragraph that describes Fig. 7b.";

In column 9, line 21, please delete the words "—has been inserted after the paragraph that describes Fig. 9.";

Signed and Sealed this

Fifth Day of December, 2006

JON W. DUDAS
*Director of the United States Patent and Trademark Office*